(12) United States Patent
Ioka

(10) Patent No.: US 10,694,100 B2
(45) Date of Patent: Jun. 23, 2020

(54) IMAGE PROCESSING APPARATUS, IMAGE PROCESSING METHOD, AND COMPUTER READABLE RECORDING MEDIUM

(71) Applicant: OLYMPUS CORPORATION, Hachioji-shi, Tokyo (JP)

(72) Inventor: Ken Ioka, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 21 days.

(21) Appl. No.: 16/220,604

(22) Filed: Dec. 14, 2018

(65) Prior Publication Data

US 2019/0124258 A1 Apr. 25, 2019

Related U.S. Application Data

(63) Continuation of application No. PCT/JP2016/068442, filed on Jun. 21, 2016.

(51) Int. Cl.
*A61B 1/04* (2006.01)
*H04N 5/232* (2006.01)
(Continued)

(52) U.S. Cl.
CPC ..... *H04N 5/23229* (2013.01); *A61B 1/00009* (2013.01); *G06T 3/4007* (2013.01);
(Continued)

(58) Field of Classification Search
CPC ........ H04N 5/3537; G06T 2207/30004; G06T 5/009; G06T 7/0012; A61B 1/04; A61B 1/00004; A61B 1/00006; A61B 1/00009
See application file for complete search history.

(56) References Cited

U.S. PATENT DOCUMENTS

2011/0071352 A1 3/2011 Ozawa et al.
2011/0176730 A1* 7/2011 Sasaki ................... G06T 3/4015
382/167
(Continued)

FOREIGN PATENT DOCUMENTS

JP 2012005807 A 1/2012
JP 2012125462 A 7/2012
(Continued)

OTHER PUBLICATIONS

International Search Report (ISR) dated Sep. 20, 2016 issued in International Application No. PCT/JP2016/068442.
(Continued)

*Primary Examiner* — Kelly L Jerabek
(74) *Attorney, Agent, or Firm* — Holtz, Holtz & Volek PC

(57) ABSTRACT

An image processing apparatus includes: a processor configured to execute: acquiring image data; generating a first interpolation image data corresponding to light in a red wavelength band, a second interpolation image data corresponding to light in a green wavelength band, a third interpolation image data corresponding to light in a blue wavelength band, and fourth interpolation image data corresponding to narrow band light; calculating a ratio of a pixel value of the fourth interpolation image data to a pixel value of the second interpolation image data for each region including one or a plurality of pixels; extracting a pixel of the fourth interpolation image data in the region where the calculated ratio exceeds a predetermined threshold value; generating a composite image data based on the pixel value of the extracted pixel and the second or the third interpolation image data; and generating color image data.

9 Claims, 17 Drawing Sheets

(51) Int. Cl.
- *H04N 9/04* (2006.01)
- *A61B 1/00* (2006.01)
- *H04N 9/73* (2006.01)
- *G06T 3/40* (2006.01)
- *H01L 27/146* (2006.01)
- *H04N 5/341* (2011.01)
- *A61B 1/06* (2006.01)

(52) U.S. Cl.
CPC ....... *H01L 27/14605* (2013.01); *H04N 5/341* (2013.01); *H04N 9/04513* (2018.08); *H04N 9/04559* (2018.08); *H04N 9/73* (2013.01); *A61B 1/00186* (2013.01); *A61B 1/063* (2013.01); *A61B 1/0638* (2013.01)

(56) References Cited

U.S. PATENT DOCUMENTS

| | | | |
|---|---|---|---|
| 2012/0053434 A1* | 3/2012 | Saito | A61B 1/00009 600/324 |
| 2012/0154565 A1 | 6/2012 | Kaku | |
| 2012/0154566 A1 | 6/2012 | Kaku | |
| 2012/0257030 A1* | 10/2012 | Lim | A61B 1/00009 348/70 |
| 2014/0046131 A1* | 2/2014 | Morita | A61B 1/00179 600/109 |
| 2014/0316195 A1 | 10/2014 | Kaku et al. | |
| 2015/0092034 A1* | 4/2015 | Iwane | H04N 5/243 348/68 |
| 2015/0112128 A1* | 4/2015 | Yoshino | A61B 1/00009 600/103 |
| 2017/0258304 A1 | 9/2017 | Ioka et al. | |
| 2019/0069766 A1* | 3/2019 | Mizukura | A61B 1/0623 |
| 2019/0125174 A1* | 5/2019 | Makino | A61B 1/00 |

FOREIGN PATENT DOCUMENTS

| | | |
|---|---|---|
| JP | 2013081709 A | 5/2013 |
| JP | 2013150712 A | 8/2013 |
| JP | 5501210 B2 | 3/2014 |
| WO | 2016088269 A1 | 6/2016 |

OTHER PUBLICATIONS

Written Opinion dated Sep. 20, 2016 issued in International Application No. PCT/JP2016/068442.

* cited by examiner

FIG.15

| | | F1 |
|---|---|---|
| 0 | -1 | 0 |
| -1 | 4 | -1 |
| 0 | -1 | 0 | ns
IMAGE PROCESSING APPARATUS, IMAGE PROCESSING METHOD, AND COMPUTER READABLE RECORDING MEDIUM

CROSS-REFERENCE TO RELATED APPLICATION

This application is a continuation of International Application No. PCT/JP2016/068442, filed on Jun. 21, 2016, the entire contents of which are incorporated herein by reference.

BACKGROUND

The present disclosure relates to an image processing apparatus, an image processing method, and a computer readable recording medium.

In recent years, as an observation method of an endoscope, a white light observation method using white illumination light (white light) and a narrow band light observation method using illumination light (hereinafter referred to as "special light") including two narrow band light beams included in blue and green wavelength bands are widely known. Among these methods, the narrow band light observation method can obtain an image that highlights capillaries, the microscopic pattern of a mucosa, and the like that are present in the mucosal surface layer of a living body.

As an endoscope that performs such a narrow band light observation method, there has been known a technique with which information on a special light observation image captured with special light is combined with one normal light observation image captured with white light, whereby capillaries, the microscopic pattern of a mucosa, and the like that are present in the mucosal surface layer of a living body is observed using one observation image (see Japanese Patent No. 5501210). With this technique, frequency processing using a filter such as a high-pass filter or a band-pass filter is performed on the special light observation image, whereby capillaries are extracted from the special light observation image and an extracted result is combined with the normal light observation image to generate an observation image.

SUMMARY

An image processing apparatus according to one aspect of the present disclosure includes: a processor comprising hardware, the processor being configured to execute: acquiring image data generated by an imaging device having a predetermined array pattern including a first pixel configured to receive light in a red wavelength band, a second pixel configured to receive light in a green wavelength band, a third pixel configured to receive light in a blue wavelength band, and a fourth pixel configured to receive at least one of: narrow band light in a wavelength band that is the green wavelength band and narrower than the green wavelength band; and narrow band light in a wavelength band that is the blue wavelength band and narrower than the blue wavelength band; generating, by performing demosaicing processing of interpolating a pixel value to the acquired image data, a first interpolation image data corresponding to the light in the red wavelength band, a second interpolation image data corresponding to the light in the green wavelength band, a third interpolation image data corresponding to the light in the blue wavelength band, and fourth interpolation image data corresponding to the narrow band light; calculating: a ratio of a pixel value of the fourth interpolation image data to a pixel value of the second interpolation image data for each region including one or a plurality of pixels based on the second interpolation image data and the fourth interpolation image data corresponding to the narrow band light in the wavelength band that is the green wavelength band and narrower than the green wavelength band; or a ratio of a pixel value of the fourth interpolation image data to a pixel value of the third interpolation image data for each region including one or a plurality of pixels based on the third interpolation image data and the fourth interpolation image data corresponding to the narrow band light in the wavelength band that is the blue wavelength band and narrower than the blue wavelength band; extracting a pixel of the fourth interpolation image data in the region where the calculated ratio exceeds a predetermined threshold value; generating a composite image data based on at least one of: the pixel value of the extracted pixel of the fourth interpolation image data corresponding to the narrowband light in the wavelength band that is the green wavelength band and narrower than the green wavelength band and the second interpolation image data; and the extracted pixel value of the pixel of the fourth interpolation image data corresponding to the narrow band light in the wavelength band that is the blue wavelength band and narrower than the blue wavelength band and the third interpolation image data; and generating color image data based on the generated composite image data, the first interpolation image data, and at least one of the second interpolation image data and the third interpolation image data.

The above and other features, advantages and technical and industrial significance of this disclosure will be better understood by reading the following detailed description of presently preferred embodiments of the disclosure, when considered in connection with the accompanying drawings.

BRIEF DESCRIPTION OF THE DRAWINGS

FIG. 15 is a diagram for schematically describing a Laplacian filter used by an edge extraction unit according to the second embodiment;

DETAILED DESCRIPTION

Figure 1:
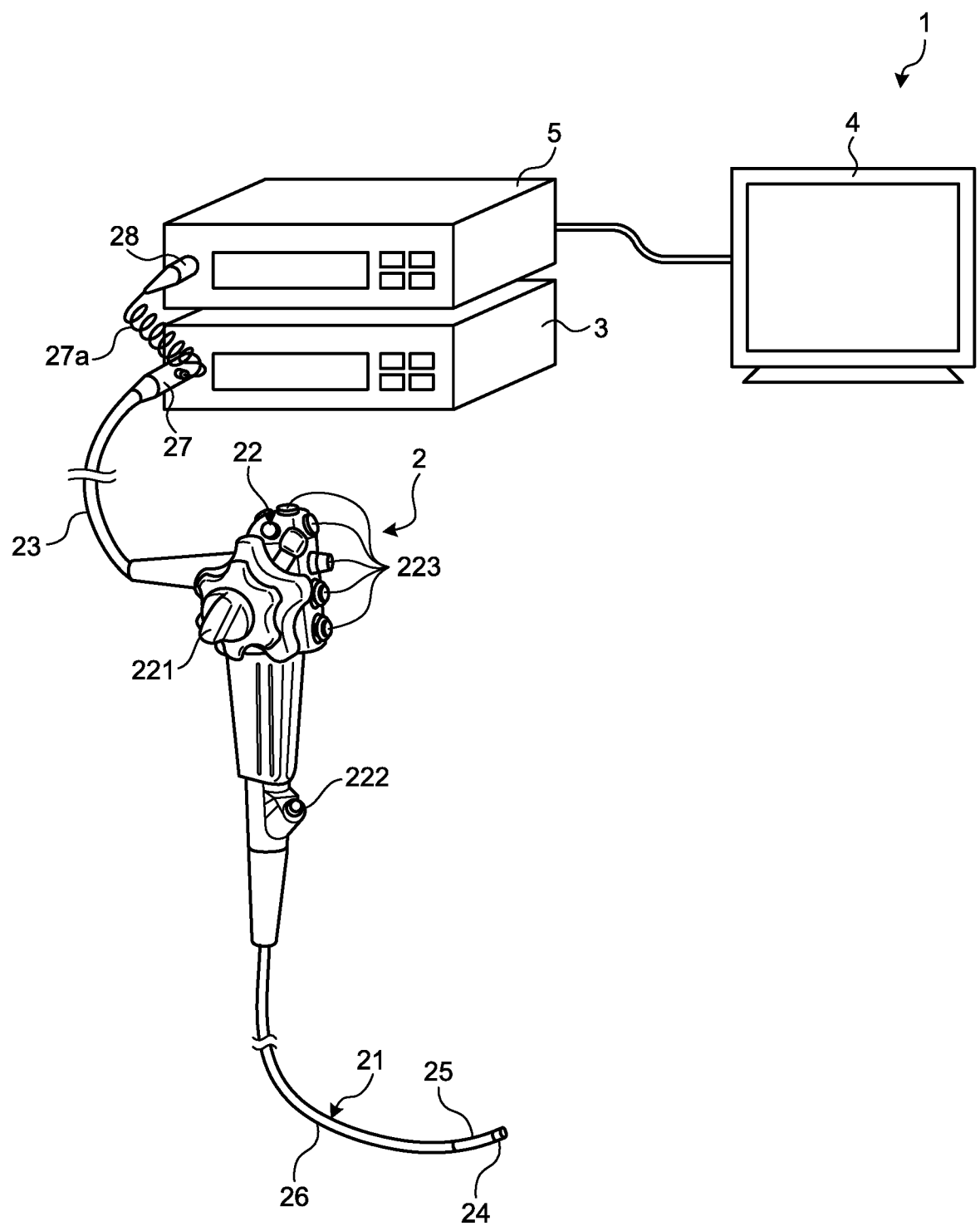
FIG. 1 is a diagram schematically illustrating an overall configuration of an endoscope system according to a first embodiment.

Hereinafter, modes for carrying out the present disclosure (hereinafter referred to as "embodiments") will be described with reference to the accompanying drawings. In the present embodiment, an endoscope system for medical use that captures an image in a body cavity of a subject such as a patient to display the image will be described as an example. Note that the present disclosure is not limited to these embodiments. Furthermore, in the description of the drawings, the same components are added with the same reference numerals.

First Embodiment

Configuration of Endoscope System

FIG. 1 is a diagram schematically illustrating an overall configuration of an endoscope system according to a first embodiment. The endoscope system 1 illustrated in FIG. 1 includes an endoscope 2 (scope) that captures an in-vivo image of a subject by being inserted into a body cavity of the subject, and a light source device 3 that generates illumination light to be emitted from a distal end of the endoscope 2, a display device 4 that displays an image corresponding to image data captured by the endoscope 2, a processor 5 (control device) that performs predetermined image processing on the in-vivo image captured by the endoscope 2 and causes the display device 4 to display the result, and comprehensively controls the operation of the whole of the endoscope system 1.

The endoscope 2 includes an insertion unit 21 having an elongated shape having flexibility, an operating unit 22 connected to the proximal end side of the insertion unit 21 and that receives inputs of various operation signals, and a universal cord 23 extending from the operating unit 22 in a direction different from a direction in which an insertion unit 21 extends, the universal cord 23 incorporating various cables connected to the processor 5 and the light source device 3.

The insertion unit 21 includes a distal end portion 24 incorporating an imaging device (imaging unit) described later, a bending portion 25 that is bendable and includes a plurality of bending pieces, and a tube portion 26 connected to a proximal end side of the bending portion 25 and having an elongated shape having flexibility.

The operating unit 22 includes a bending knob 221 that bends the bending portion 25 in an up and down direction and a left and right direction, a treatment tool insertion unit 222 that inserts a treatment tool such as a biopsy forceps, a laser knife, and an examination probe into the body cavity, and a plurality of switches 223 that are operation input units with which operation instruction signals of peripheral devices such as an air sending unit, a water sending unit, and a gas sending unit in addition to the light source device 3 and the processor 5 are input. A treatment tool inserted from the treatment tool insertion unit 222 is exposed from an opening (not illustrated) via the distal end portion 24.

The universal cord 23 incorporates at least a light guide and a collective cable. The universal cord 23 includes a connector unit 27 (see FIG. 1) attachable to and detachable from the light source device 3. The connector unit 27 includes a coil cable 27a that has a coil shape and extends therefrom and an electric connector unit 28 attachable to and detachable from the processor 5 at an extending end of the coil cable 27a. The connector unit 27 is configured using a field programmable gate array (FPGA).

The light source device 3 is configured using, for example, a halogen lamp and a white light emitting diode (LED). Under the control of the processor 5, the light source device 3 emits illumination light toward a subject from a distal end side of an insertion portion of the endoscope 2.

Under the control of the processor 5, the display device 4 displays an image corresponding to an image signal that has subjected to the image processing by the processor 5 and various information on the endoscope system 1. The display device 4 is configured using a display panel such as liquid crystal display panel and an organic electro luminescence (EL) display panel.

The processor 5 performs the predetermined image processing on RAW image data input from the endoscope 2 and outputs the RAW image data to the display device 4. The processor 5 is configured using a central processing unit (CPU) or the like.

Figure 2:
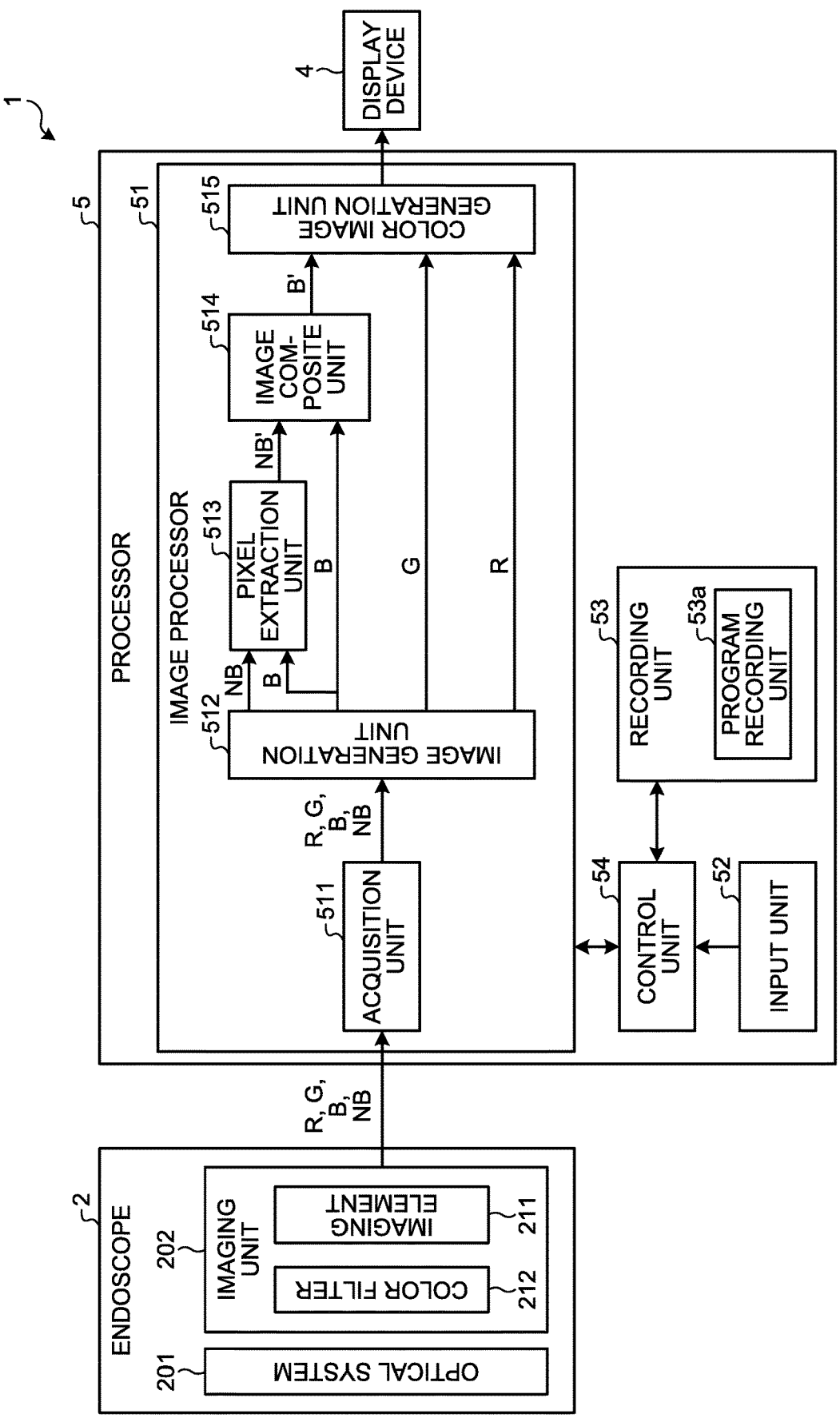
FIG. 2 is a block diagram illustrating functions of a main part of the endoscope system according to the first embodiment.

Next, functions of a main part of the endoscope system 1 will be described. FIG. 2 is a block diagram illustrating functions of a main part of the endoscope system 1. The details of each part of the endoscope system 1 and the path of the electric signal in the endoscope system 1 will be described with reference to FIG. 2.

Configuration of Endoscope

First, the configuration of the endoscope 2 will be described.

As illustrated in FIG. 2, the endoscope 2 includes an optical system 201 and an imaging unit 202.

The optical system 201 forms a subject image by receiving reflected light of the illumination light emitted by the light source device 3 on an imaging surface of the imaging unit 202. The optical system 201 is configured using one or a plurality of lenses, prisms, and the like.

Under the control of the processor 5, the imaging unit 202 receives the subject image formed on a light receiving surface by the optical system 201 and performs a photoelectric conversion, thereby generating image data (RAW image data) of the subject and outputs this generated image data to the processor 5. Specifically, the imaging unit 202 captures the image of the subject at a reference frame rate, for example, at a frame rate of 60 fps, and generates image data of the subject. The imaging unit 202 includes an imaging element 211 and a color filter 212.

The imaging element 211 is configured using an imaging sensor such as a charge coupled device (CCD) and a complementary metal oxide semiconductor (CMOS) that photoelectrically converts light received by a plurality of pixels arranged in a two-dimensional lattice shape to generate an electric signal.

The color filter 212 is configured using a filter unit that includes a wide band filter R that transmits light in a red wavelength band, a wide band filter G that transmits light in a green wavelength band, a wide band filter B that transmits light in a blue wavelength band, and a narrow band filter NB that transmits light in a wavelength band that is the blue wavelength band and narrower than the blue wavelength band, and the color filter 212 is formed by arranging this filter unit so as to correspond to the pixels of the imaging element 211.

Figure 3:
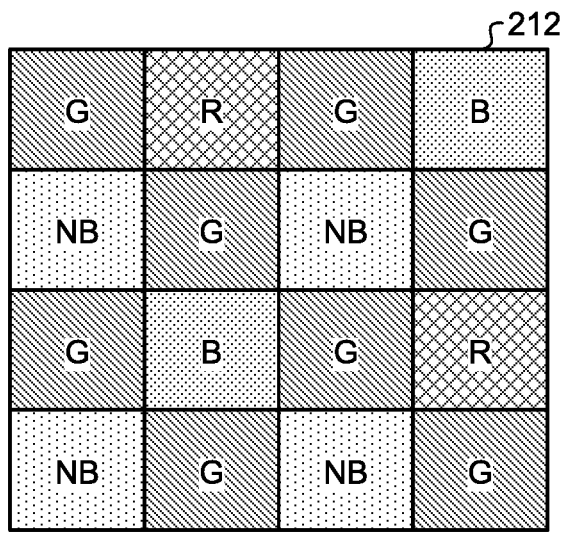
FIG. 3 is a diagram schematically illustrating a configuration of a color filter according to the first embodiment.

FIG. 3 is a diagram schematically illustrating a configuration of the color filter 212. As illustrated in FIG. 3, the color filter 212 is configured using the filter unit that forms a predetermined array pattern in which two wide band filters R that transmits a red component, eight wide band filters G that transmit a green component, two wide band filters B that transmit a blue element, and four narrow band filters NB that transmit light in a narrow band are one set. The color filter 212 is arranged at a position corresponding to any of the plurality of pixels of the imaging element 211 in which the individual filters forming the above-described array pattern are arrayed in a two-dimensional lattice shape. Here, the peak wavelength of the wavelength band of light in the narrow band in the first embodiment is in the range of 395 nm to 435 nm. The image data generated by the imaging element 211 using the color filter 212 configured as described above is subjected to predetermined image processing by the processor 5 described later, thereby being converted into a color image.

Figure 4:
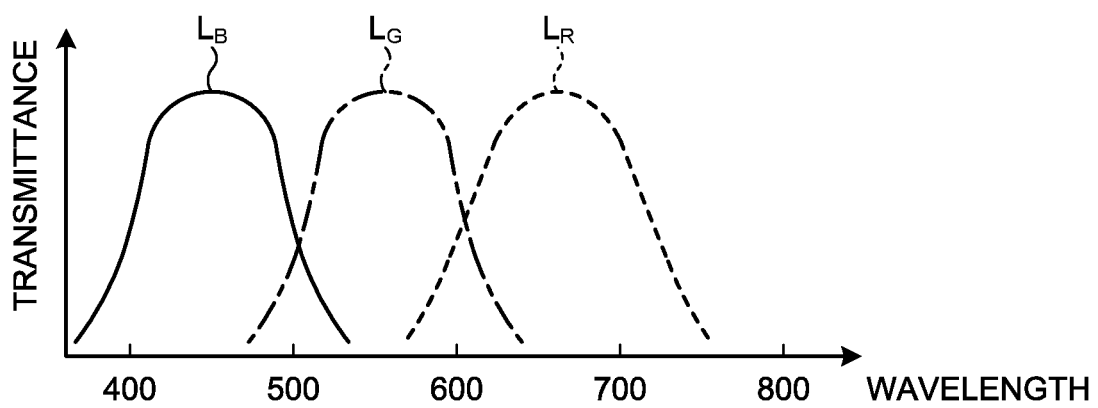
FIG. 4 is a graph illustrating a relationship between transmittance and a wavelength of each wide band filter constituting the color filter according to the first embodiment.
Figure 5:
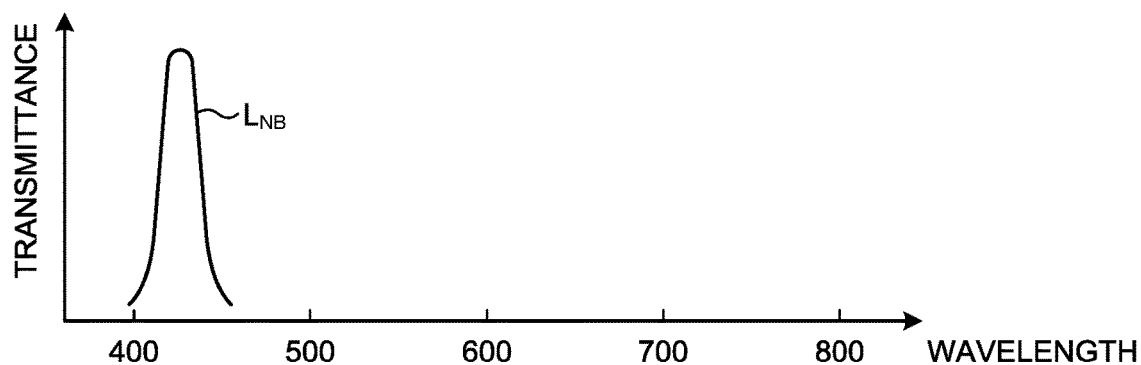
FIG. 5 is a graph illustrating a relationship between transmittance and a wavelength of a narrow band filter constituting the color filter according to the first embodiment.

FIG. 4 is a graph illustrating a relationship between transmittance and a wavelength of each wide band filter constituting the color filter 212. FIG. 5 is a graph illustrating a relationship between transmittance and a wavelength of the narrow band filter NB constituting the color filter 212. In FIGS. 4 and 5, a horizontal axis indicates the wavelength (nm) and a vertical axis indicates the transmittance. In FIG. 4, a curve $L_B$ indicates a relationship between transmittance and the wavelength of the wide band filter B, a curve $L_G$ indicates a relationship between transmittance and a wavelength of the wide band filter G, a curve $L_R$ indicates a relationship between transmittance and a wavelength of the wide band filter R. Furthermore, in FIG. 5, a curve $L_{NB}$ indicates a relationship between transmittance and a wavelength of the narrow band filter NB. Furthermore, in FIG. 5, a case where the peak wavelength of the narrow band filter NB is in the range of 395 nm to 435 nm will be described.

As illustrated in FIGS. 4 and 5, the spectral characteristics of the narrow band filter NB are narrower than those of the spectral characteristics of the wide band filter B and are included in the wavelength band of the wide band filter B. Note that, hereinafter, a pixel in which the wide band filter R is arranged is called an R pixel (first pixel), a pixel in which the wide band filter G is arranged is called a G pixel (second pixel), and a pixel in which the wide band filter B is arranged is called a B pixel (third pixel), a pixel in which the narrow band filter NB is arranged is called an NB pixel (fourth pixel).

Configuration of Processor

Next, a configuration of the processor 5 will be described.

As illustrated in FIG. 2, the processor 5 includes an image processor 51, an input unit 52, a recording unit 53, and a control unit 54.

The image processor 51 is configured using a graphics processor (GPU) or the like, acquires image data generated by the endoscope 2, performs predetermined image processing on the acquired image data, and outputs the image data to the display device 4. The image processor 51 includes an acquisition unit 511, an image generation unit 512, a pixel extraction unit 513, an image composite unit 514, and a color image generation unit 515. Note that in the first embodiment, the image processor 51 functions as an image processing apparatus.

The acquisition unit 511 acquires the image data generated by the endoscope 2 and outputs the acquired image data to the image generation unit 512. Specifically, the acquisition unit 511 acquires pixel values (pixel value R, pixel value G, pixel value B, and pixel value NB) of the R pixel, the G pixel, the B pixel, and the NB pixel that constitute an image corresponding to the image data generated by the endoscope 2 from the imaging element 211 and outputs the acquired pixel value of each pixel to the image generation unit 512.

The image generation unit 512 performs known demosaicing processing of interpolating the pixel value of the pixel whose pixel value is missing, based on the pixel value of each pixel (each channel) input from the acquisition unit 511, thereby generating each of an R image (first interpolation image data) corresponding to the light in the red wavelength band, a G image (second interpolation image data) corresponding to the light in the green wavelength band, a B image (third interpolation image data) corresponding to the light in the blue wavelength band, and an NB image (fourth interpolation image data) corresponding to narrow band light. The image generation unit 512 outputs the NB image and the B image to the pixel extraction unit 513 and outputs the B image to the image composite unit 514. Furthermore, the image generation unit 512 outputs the G image and the R image to the color image generation unit 515.

The pixel extraction unit 513 generates an NB' image by extracting a feature area of or a pixel group of the NB image based on the NB image and the B image that are input from the image generation unit 512 and outputs the generated NB' image to the image composite unit 514. Specifically, the pixel extraction unit 513 calculates a ratio between a pixel value (signal value) of the NB image and a pixel value (signal value) of the B image for each area from one or a plurality of pixels based on the NB pixel and the B image, extracts the pixel of the NB image, the ratio of which is equal to or larger than a predetermined threshold value, and outputs the pixel to the image composite unit 514. More specifically, the pixel extraction unit 513 calculates the ratio (NB/B) of the pixel value of the NB image to the pixel value of the B image for each pixel based on the NB pixel and the B image and outputs the pixel and the pixel position (pixel address) of the NB image, the ratio of which is equal to or larger than the predetermined threshold value, to the image composite unit 514.

Figure 6:
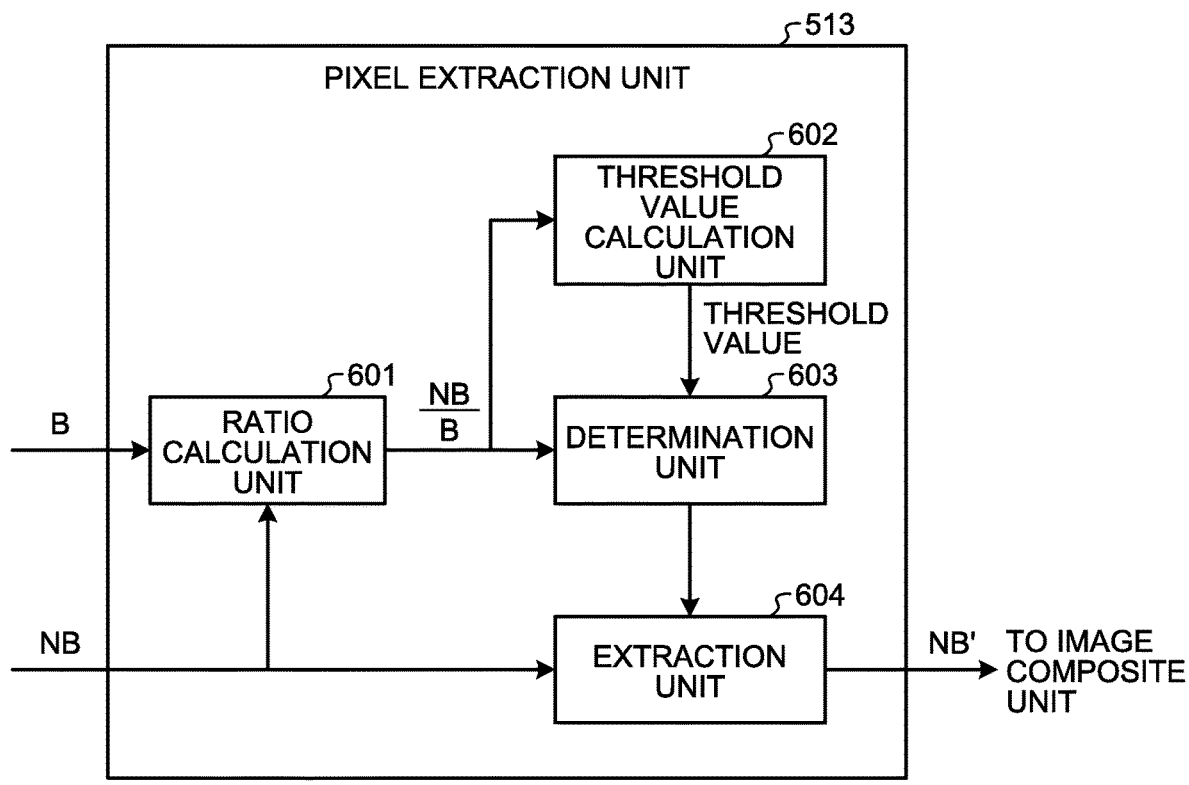
FIG. 6 is a block diagram illustrating a detailed configuration of a pixel extraction unit according to the first embodiment.

FIG. 6 is a block diagram illustrating a detailed configuration of the pixel extraction unit 513. As illustrated in FIG. 6, the pixel extraction unit 513 includes a ratio calculation unit 601, a threshold value calculation unit 602, a determination unit 603, and an extraction unit 604.

The ratio calculation unit 601 calculates the ratio (NB/B) of the pixel value of the NB image to the pixel value of the B image for each pixel based on the NB image and the B image that are input from the image generation unit 512 and outputs this calculation result to each of the threshold value calculation unit 602 and the determination unit 603.

The threshold value calculation unit 602 generates a histogram of the calculation result of the ratio (NB/B) of the pixel value of the NB image to the pixel value of the B image input from the ratio calculation unit 601 and calculates a threshold value based on this histogram.

Figure 7:
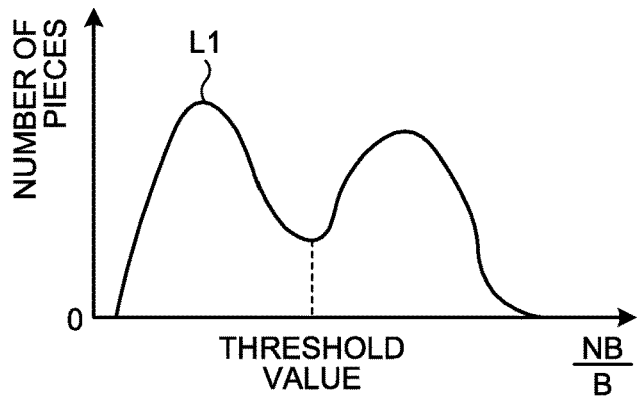
FIG. 7 is a diagram schematically illustrating an example of a histogram calculated by a threshold value calculation unit according to the first embodiment.

FIG. 7 is a graph schematically illustrating an example of the histogram. In FIG. 7, a horizontal axis indicates the ratio (NB/B) and a vertical axis indicates the number of pieces (the number of pixels). Furthermore, in FIG. 7, a curve L1 indicates the histogram. As indicated by the curve L1 in FIG. 7, the calculation results of the ratio calculation unit 601 forms a bimodal histogram. Therefore, the threshold value calculation unit 602 calculates the ratio (minimum value) corresponding to the valley of the curve L1 as the threshold value.

The determination unit 603 determines whether the ratio (NB/B) of the pixel values input from the ratio calculation unit 601 for each pixel is equal to or larger than the threshold value calculated by the threshold value calculation unit 602 and outputs this determination result to the extraction unit 604.

The extraction unit 604 extracts a pixel having a feature included in the NB image based on the determination result input from the determination unit 603 and the NB image input from the image generation unit 512. Specifically, the extraction unit 604 extracts the pixel determined as being equal to or larger than the threshold value by the determination unit 603. More specifically, the extraction unit 604 outputs the pixel determined as being equal to or larger than the threshold value by the determination unit 603 to the image generation unit 512, while maintaining a pixel value of a pixel corresponding to a pixel position of the pixel determined as being equal to or larger than the threshold value by the determination unit 603. Also, the extraction unit 604 outputs, as 0, a pixel value of a pixel corresponding to a pixel position of a pixel determined as being not equal to or larger than the threshold value by the determination unit 603 to the image generation unit 512, thereby extracting the pixel having a feature included in the NB image to generate an NB' image and outputting the NB' image to the image generation unit 512.

The image composite unit 514 adds (combines) the NB' image input from the pixel extraction unit 513 to (with) the B image input from the image generation unit 512, thereby generating a composite image B' (composite image data). Specifically, the image composite unit 514 adds the pixel value of each pixel constituting the NB' image to the pixel value of each pixel constituting the B pixel, thereby generating a composite image B' and outputting this composite image B' to the color image generation unit 515.

The color image generation unit 515 generates a color image based on the G image and the R image that are input from the image generation unit 512 and the composite image B' input from the image composite unit 514 and outputs the color image to the display device 4. Specifically, the color image generation unit 515 combines the pixel value of each pixel constituting the G image, the pixel value of each pixel constituting the R image, and the pixel value of each pixel constituting the composite image B' to generate a color image and outputs this color image to the display device 4.

Referring back to FIG. 2, description of the configuration of the processor 5 will be continued.

The input unit 52 is configured using a button, a switch, and the like, and receives inputs of instruction signals instructing various kinds of processing to be executed by the endoscope system 1 and a change signal for changing a parameter.

The recording unit 53 is configured using a read only memory (ROM), a random access memory (RAM), or the like and records image data generated by the endoscope 2, programs executed by the endoscope system 1, and information under processing. Furthermore, the recording unit 53 has a program recording unit 53a that records the programs executed by the endoscope system 1.

The control unit 54 is configured using a CPU or the like and controls each unit constituting the endoscope system 1 in a comprehensive manner. The control unit 54 controls the emission timing of the illumination light of the light source device 3, the imaging timing of the imaging unit 202 of the endoscope 2, and the like.

Processing by Processor

Figure 8:
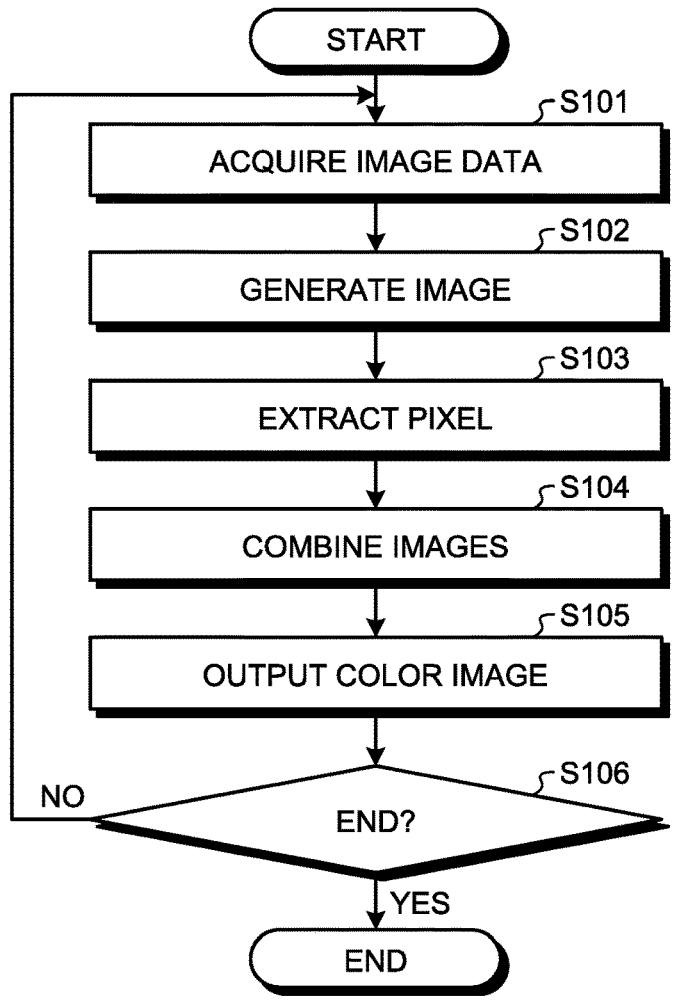
FIG. 8 is a flowchart illustrating an overview of processing executed by a processor according to the first embodiment.

Next, processing executed by the processor 5 will be described. FIG. 8 is a flowchart illustrating an overview of the processing executed by the processor 5.

As illustrated in FIG. 8, first, the acquisition unit 511 acquires the image data generated by the endoscope 2 from the endoscope 2 (step S101). In this case, the acquisition unit 511 outputs the image data acquired from the endoscope 2 to the image generation unit 512.

Subsequently, the image generation unit 512 performs the demosaicing processing based on the pixel value of each pixel input from the acquisition unit 511, thereby generating an image corresponding to each color channel (step S102). Specifically, the image generation unit 512 generates each of the R image, the G image, the B image, and the NB image.

Thereafter, the pixel extraction unit 513 extracts a pixel having a feature of the NB image based on the NB image and the B image that are input from the image generation unit 512 (step S103). Specifically, the pixel extraction unit 513 calculates the ratio of the pixel value of the NB image to the pixel value of the B image for each pixel based on the NB pixel and the B image and outputs a pixel, the ratio of which is equal to or larger than the predetermined threshold value, to the image composite unit 514.

Subsequently, the image composite unit 514 combines the NB' image input from the pixel extraction unit 513 with the B image input from the image generation unit 512 (step S104). Specifically, the image composite unit 514 adds the pixel value of each pixel constituting the NB' image to the pixel value of each pixel constituting the B pixel for each pixel, thereby generating a composite image B' and outputs this composite image B' to the color image generation unit 515.

Thereafter, based on the G image and the R image that are input from the image generation unit 512 and the composite image 5' input from the image composite unit 514, the color image generation unit 515 generates a color image and outputs it to the display device 4 (step S105).

Subsequently, in a case where an instruction signal instructing the end of the examination by the endoscope system 1 has been input (step S106: Yes), the processor 5 ends the present processing. Meanwhile, in a case where the instruction signal instructing the end of the examination by the endoscope system 1 has not been input (step S106: No), the processor 5 returns to above-described step S101.

According to the first embodiment described above, the pixel extraction unit 513 calculates the ratio of the pixel value of the NB image to the pixel value of the B image for each pixel based on the NB pixel and the B image, outputs the pixel value of the pixel, the ratio of which is equal to or larger than a predetermined threshold value, to the image composite unit 514, and the image composite unit 514 adds the pixel value of each pixel constituting the NB' image to the pixel value of each pixel constituting the B pixel for each pixel, whereby generating a composite image B' and outputting this composite image B' to the color image generation unit 515. Therefore, even in a case where a special light observation image is combined with a normal light observation image, a desired observation image can be obtained.

Note that according to the first embodiment, the ratio calculation unit 601 calculates the ratio between the pixel value of the NB image and the pixel value of the B image for each pixel. However, the ratio calculation unit 601 may divide the NB image and the B pixel into a plurality of blocks every predetermined number of pixels (for example, every ten pixels) and calculate a ratio between an average value of the pixel values of respective pixels included in the block of the B image and an average value of the pixel values of respective pixels included in the block of the NB image for each block. In this case, the extraction unit 604 may extract a pixel included in the block of the NB image determined as having been exceeded the threshold value by the determination unit 603. As a result, it is possible to reduce a calculation amount of the ratio calculation unit 601.

Modification of First Embodiment

Next, a modification of the first embodiment will be described. The modification of the first embodiment is different from the configuration of the image processor 51 according to the above-described first embodiment. Hereinafter, the configuration of an endoscope system according to the modification of the first embodiment will be described. Note that the same components as those of the above-described first embodiment are denoted by the same reference numerals, and the description thereof is omitted.

Configuration of Endoscope System

Figure 9:
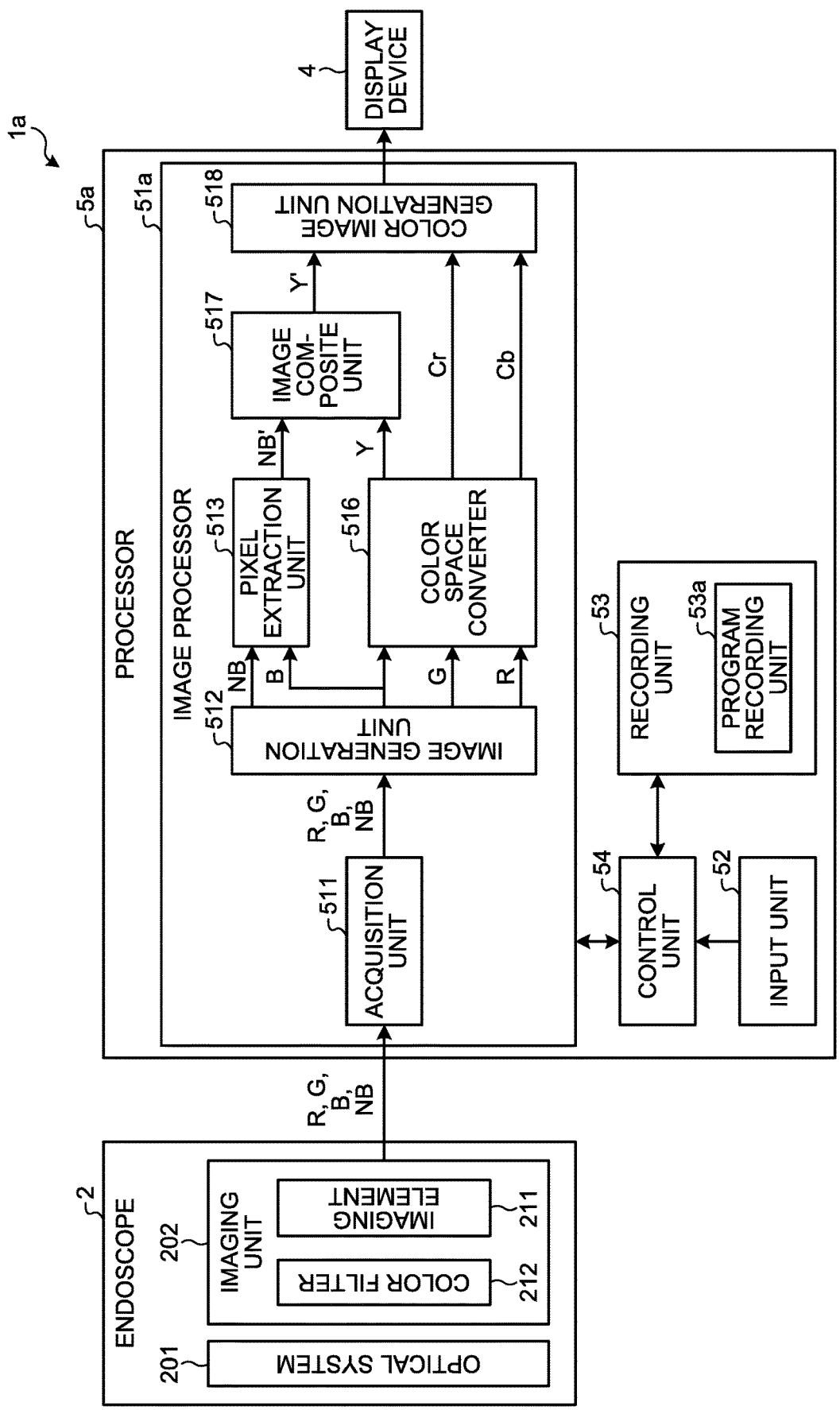
FIG. 9 is a block diagram illustrating functions of a main part of an endoscope system according to a modification of the first embodiment.

FIG. 9 is a block diagram illustrating functions of a main part of the endoscope system according to the modification of the first embodiment. An endoscope system 1a illustrated in FIG. 9 includes a processor 5a in place of the processor 5 of the endoscope system 1 according to the above-described first embodiment. Furthermore, the processor 5a includes an image processor 51a in place of the image processor 51 according to the above-described first embodiment.

The image processor 51a includes an acquisition unit 511, an image generation unit 512, a pixel extraction unit 513, a color space converter 516, an image composite unit 517, and a color image generation unit 518.

The color space converter 516 performs color space conversion processing on a pixel value in a red, green and blue (RGB) system of each of a B image, a G image and an R image that are input from the image generation unit 512 according to a YCbCr system to generate luminance data Y (luminance signal Y), chromaticity data Cr (chromaticity signal Cr), and chromaticity data Cb (chromaticity signal Cb). The color space converter 516 outputs the luminance data Y to the image composite unit 517 and outputs the chromaticity data Cr and the chromaticity data Cb to the color image generation unit 518.

The image composite unit 517 weights and adds an NB' image input from the pixel extraction unit 513 to the luminance data Y input from the color space converter 516, thereby generating composite luminance data Y' and outputting this composite luminance data Y' to the color image generation unit 518.

The color image generation unit 518 generates a color image based on the composite luminance data Y' input from the image composite unit 517, the chromaticity data Cr and the chromaticity data Cb that are input from the color space converter 516 and outputs the color image to a display device 4.

Processing by Processor

Figure 10:
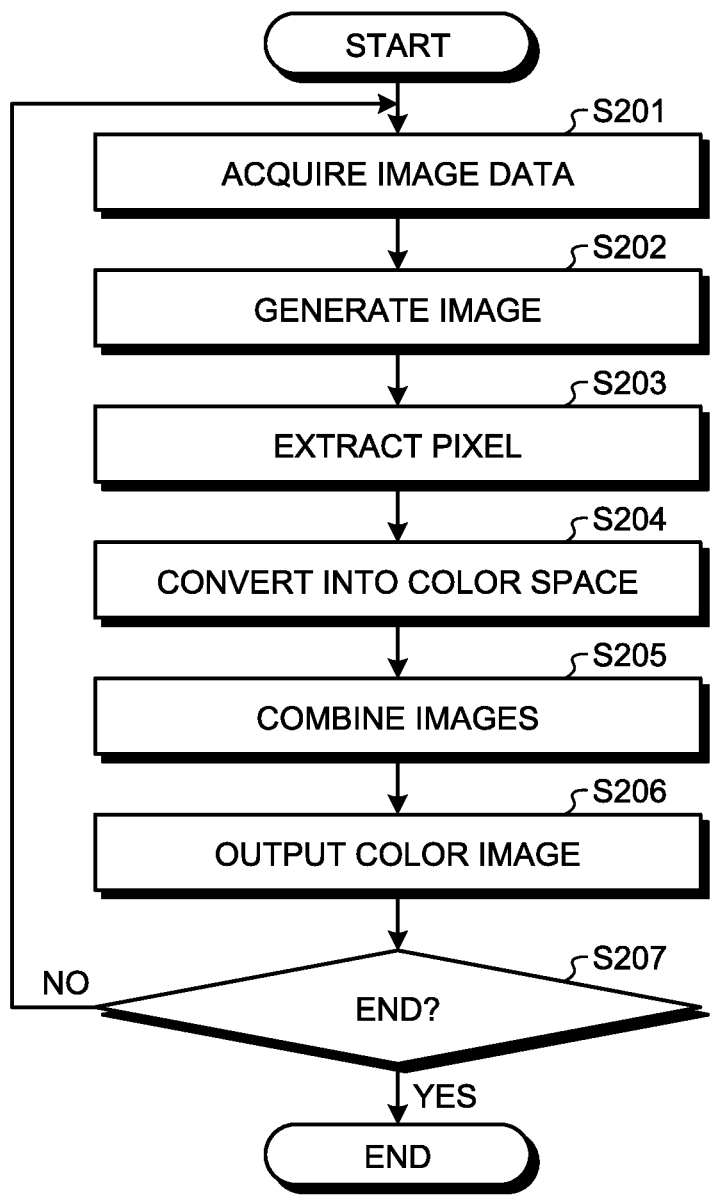
FIG. 10 is a flowchart illustrating an overview of processing executed by a processor according to a modification of the first embodiment.

Next, processing executed by the processor 5a will be described. FIG. 10 is a flowchart illustrating an overview of the processing executed by the processor 5a. In FIG. 10, steps S201 to S203 and step S207 correspond to above-described steps S101 to S103 and step S106 of FIG. 8 respectively and therefore, description thereof will be omitted.

In step S204, the color space converter 516 performs color space conversion processing on the pixel value in the RGB system of each of the B image, the G image, and the R image input from the image generation unit 512 according to the YCbCr system. Specifically, the color space converter 516 performs the color space conversion processing on the pixel value in the RGB system of each of the B image, the G image, and the R image that are input from the image generation unit 512 according to the YCbCr system to generate the luminance data Y, the chromaticity data Cr, and the chromaticity data Cb.

Subsequently, the image composite unit 517 weights and adds the NB' image input from the pixel extraction unit 513 to the luminance data Y input from the color space converter 516, thereby generating composite luminance data Y' and outputting this composite luminance data Y' to the color image generation unit 518 (step S205).

Thereafter, the color image generation unit 518 generates a color image based on the composite luminance data Y' input from the image composite unit 517, the chromaticity data Cr and the chromaticity data Cb that are input from the color space converter 516 and outputs the color image to the display device 4 (step S206). After step S206, the processor 5a proceeds to step S207.

According to the modification of the first embodiment described above, even in a case where a normal light observation image and a special light observation image are combined, a desired observation image can be obtained.

Second Embodiment

Next, a second embodiment will be described. An endoscope system according to the second embodiment is different from the configurations of the endoscope 2 and the processor 5 in the endoscope system 1 according to the above-described first embodiment and different from the processing executed by the processor 5. Specifically, in the endoscope system according to the second embodiment, a color filter includes a filter unit including narrow band filters capable of transmitting light in narrow bands different from each other. Hereinafter, a configuration of the endoscope system according to the second embodiment will be described and then the processing executed by the processor according to the second embodiment will be described. Note that the same components as those of the endoscope system 1 according to the above-described first embodiment are denoted by the same reference numerals, and the description thereof is omitted.

Configuration of Endoscope System

Figure 11:
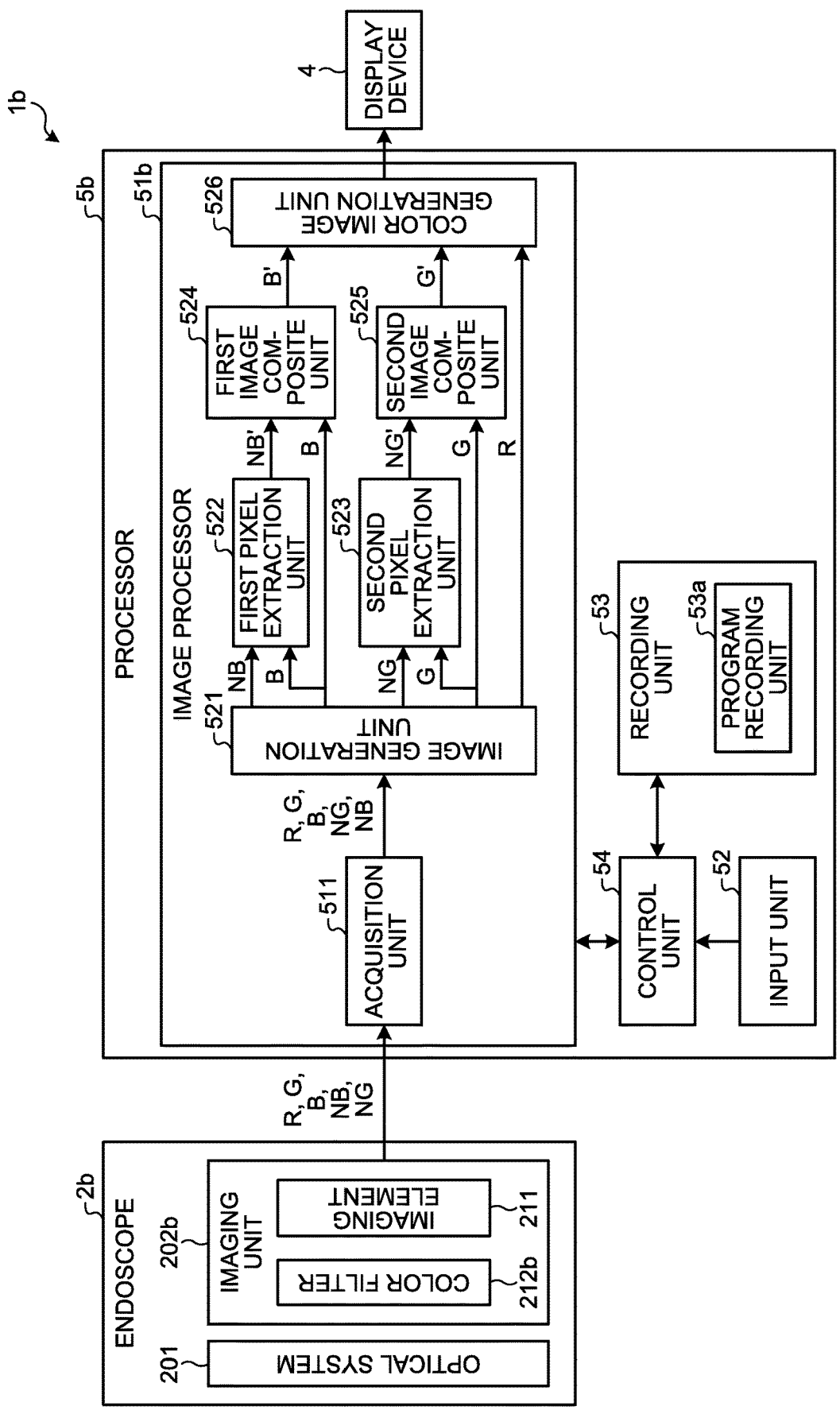
FIG. 11 is a block diagram illustrating functions of a main part of an endoscope system according to a second embodiment.

FIG. 11 is a block diagram illustrating functions of a main part of the endoscope system according to the second embodiment. An endoscope system 1b illustrated in FIG. 11 includes an endoscope 2b and a processor 5b in place of the endoscope 2 and the processor 5 of the endoscope system 1 according to the above-described first embodiment.

Configuration of Endoscope

First, the main part of the endoscope 2b will be described.

An endoscope 2b illustrated in FIG. 11 includes an imaging unit 202b in place of the imaging unit 202 of the endoscope 2 according to the above-described first embodiment. The imaging unit 202b includes a color filter 212b in place of the color filter 212 according to the above-described first embodiment.

The color filter 212b is configured using a filter unit that includes a wide band filter R that transmits light in a red wavelength band, a wide band filter G that transmits light in a green wavelength band, a wide band filter B that transmits light in a blue wavelength band, and a narrow band filter NB that transmits light in a wavelength band that is the blue wavelength band and narrower than the blue wavelength band, and a narrow band filter NG that transmits light in a wavelength band that is the green wavelength band and narrower than the green wavelength band, and the color filter 212b is formed by arranging this filter unit so as to correspond to the pixels of an imaging element 211.

Figure 12:
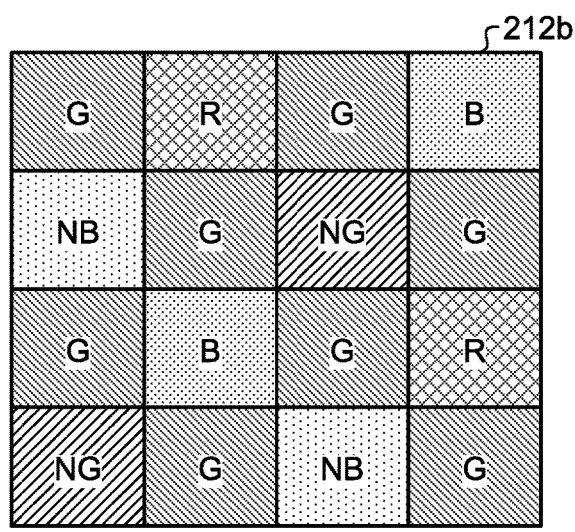
FIG. 12 is a diagram schematically illustrating a configuration of a color filter according to the second embodiment.

FIG. 12 is a diagram schematically illustrating a configuration of the color filter 212b. As illustrated in FIG. 12, the color filter 212b is configured using the filter unit that forms a predetermined array pattern in which two wide band filters R that transmit a red component, eight wide band filters G that transmit a green component, two narrow band filters B that transmit a blue element, and two narrow band filters NB that transmit light in a narrow band, and two narrow band filters NG that transmit light in a wavelength band narrower than the green wavelength band are one set. The color filter 212b is arranged at a position corresponding to any of a plurality of pixels of the imaging element 211 in which the individual filters forming the above-described array pattern are arranged in a two-dimensional lattice shape.

Figure 13:
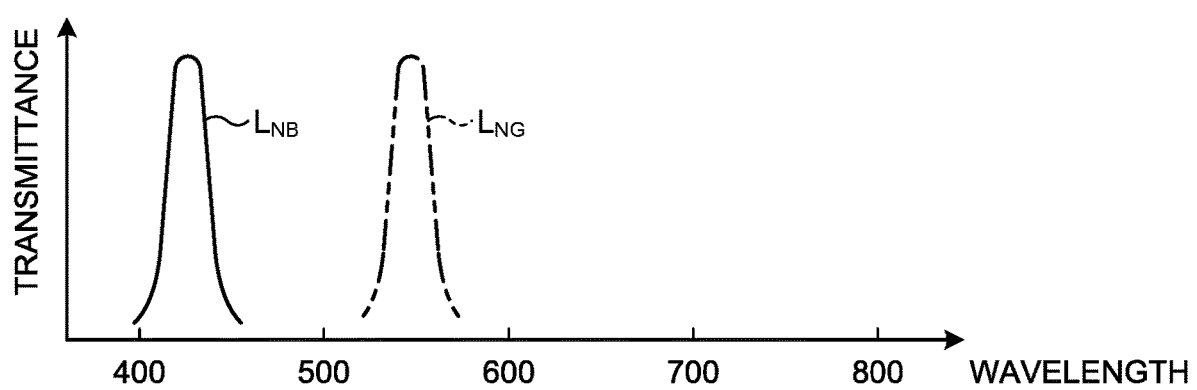
FIG. 13 is a diagram illustrating a relationship between transmittance and a wavelength of a narrow band filter constituting the color filter according to the second embodiment.

FIG. 13 is a graph illustrating a relationship between transmittance and a wavelength of the narrow band filter NB constituting the color filter 212b and a relationship between transmittance and a wavelength of the narrow band filter NG constituting the color filter 212b. In FIG. 13, a horizontal axis indicates the wavelength (nm) and a vertical axis indicates the transmittance. In FIG. 13, a curve $L_{NB}$ illustrates the relationship between the transmittance and the wavelength of the narrow band filter NB, and a curve $L_{NG}$ illustrates the relationship between the transmittance and wavelength of the narrow band filter NG. Furthermore, in FIG. 13, a case where a peak wavelength of the narrow band filter NB is in the range of 395 nm to 435 nm and a peak wavelength of the narrow band filter NG is in the range of 520 nm to 560 nm will be described.

As illustrated in FIG. 13, the spectral characteristics of the narrow band filter NB are narrower than those of the wide band filter B and are included in the wavelength band of the wide band filter B. Furthermore, the spectral characteristics of the narrow band filter NG are narrower than those of the wide band filter G and are included in the wavelength band of the wide band filter G. Hereinafter, a pixel in which the narrow band filter NG is arranged is referred to as an NG pixel.

Configuration of Processor

Next, the configuration of the processor 5b will be described.

As illustrated in FIG. 11, the processor 5b includes an image processor 51b in place of the image processor 51 of the processor 5 according to the above-described first embodiment. The image processor 51b includes an acquisition unit 511, an image generation unit 521, a first pixel extraction unit 522, a second pixel extraction unit 523, a first image composite unit 524, a second image composite unit 525, and a color image generation unit 526.

The image generation unit 521 performs known demosaicing processing based on the pixel value of each pixel (each channel) input from the acquisition unit 511, thereby generating each of an R image, a G image, a B image, an NB image, and an NG image. The image generation unit 521 outputs the NB image and the B image to the first pixel extraction unit 522 and outputs the NG image and the G image to the second pixel extraction unit 523. Furthermore, the image generation unit 521 outputs the R image to the color image generation unit 526.

The first pixel extraction unit 522 generates an NB' image by extracting a pixel having a feature of the NB image based on the NB image and the B image that are input from the image generation unit 521 and outputs the NB' image to the first image composite unit 524. Note that a detailed configuration of the first pixel extraction unit 522 will be described later.

The second pixel extraction unit 523 generates an NG' image by extracting a pixel having a feature of the NG image based on the NG image and the G image that are input from the image generation unit 521 and outputs the NG' image to the second image composite unit 525. Note that since the second pixel extraction unit 523 has a configuration similar to the configuration of the above-described first pixel extraction unit 522, the detailed description of the second pixel extraction unit 523 will be described later.

The first image composite unit 524 adds (combines) the NB' image input from the first pixel extraction unit 522 to (with) the B image input from the image generation unit 521, thereby generating a composite image B'. Specifically, the first image composite unit 524 adds the pixel value of each pixel constituting the NB' image to the pixel value of each pixel constituting the B pixel, thereby generating a composite image B' and outputting this composite image B' to the color image generation unit 526.

The second image composite unit 525 adds (combines) the NG' image input from the second pixel extraction unit 523 to (with) the G image input from the image generation unit 521, thereby generating a composite image G'. Specifically, the second image composite unit 525 adds the pixel value of each pixel constituting the NG' image to the pixel value of each pixel constituting the G pixel, thereby generating the composite image G' and outputting this composite image G' to the color image generation unit 526.

The color image generation unit 526 generates a color image based on the R image input from the image generation unit 521, the composite image B' input from the first image composite unit 524, and the composite image G' input from the second image composite unit 525 and outputs the color image to a display device 4. Specifically, the color image generation unit 526 combines the pixel value of each pixel constituting the R image, the composite image B' and the pixel value of each pixel constituting the composite image G' to generate a color image and outputs this color image to the display device 4.

Configuration of First Pixel Extracting Unit

Figure 14:
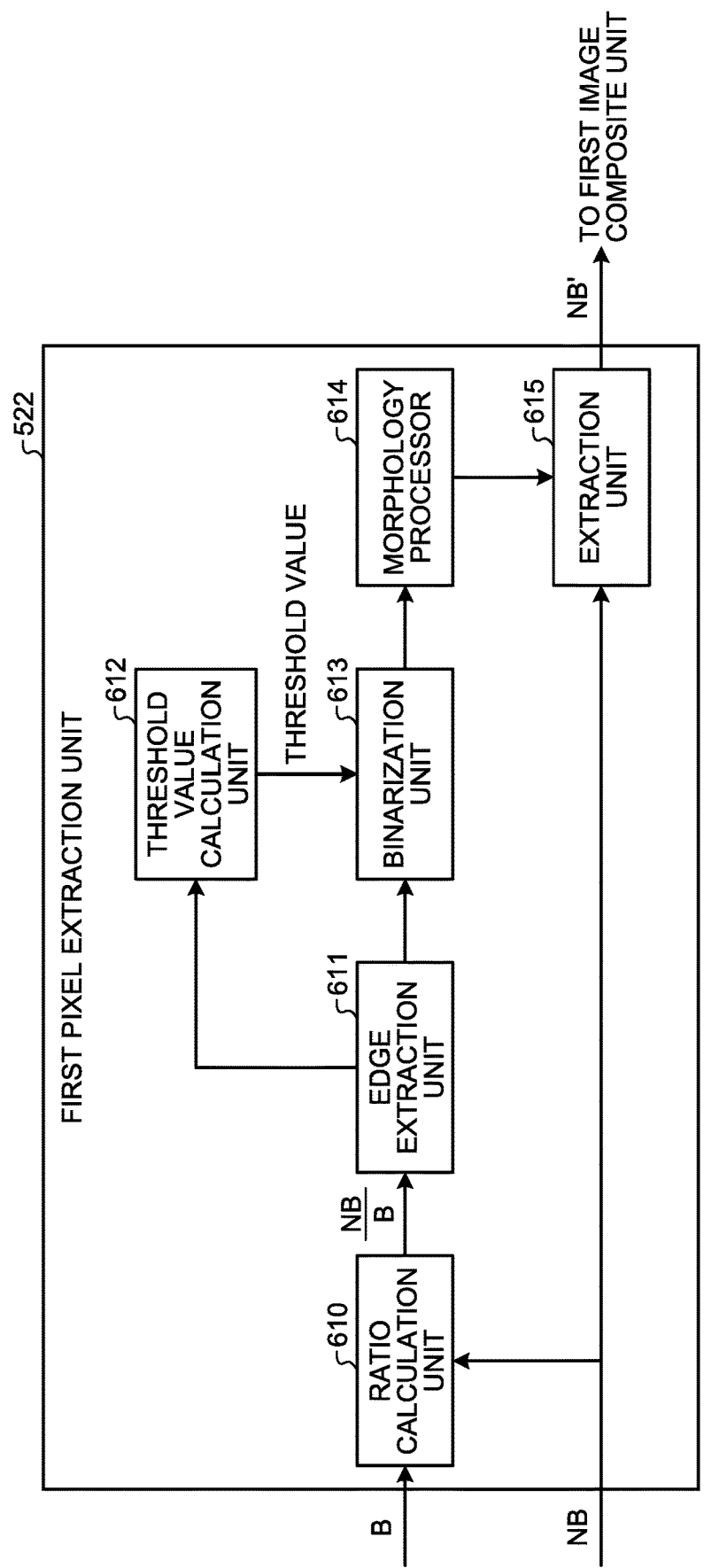
FIG. 14 is a block diagram illustrating a detailed configuration of a pixel extraction unit according to the second embodiment.

Next, a detailed configuration of the above-described first pixel extraction unit 522 will be described. FIG. 14 is a block diagram illustrating the detailed configuration of the first pixel extraction unit 522. Note that since the second pixel extraction unit 523 has a configuration similar to the configuration of the first pixel extraction unit 522, the detailed description of the second pixel extraction unit 523 will be omitted. However, the second pixel extraction unit 523 replaces the B pixel with G pixels and the NB image with the NG image, thereby having a function similar to that of the first pixel extraction unit 522.

As illustrated in FIG. 14, the first pixel extraction unit 522 includes a ratio calculation unit 610, an edge extraction unit 611, a threshold value calculation unit 612, a binarization unit 613, a morphology processor 614, and an extraction unit 615.

The ratio calculation unit 610 calculates a ratio (NB/B) of the pixel value of the B image and the pixel value of the NB image for each pixel based on the NB image and the B image that are input from the image generation unit 521 and outputs this calculation result to the edge extraction unit 611. Specifically, the ratio calculation unit 610 calculates the ratio (NB/B) of the pixel value of the NB image to the pixel value of the B image for each pixel and outputs this calculation result to the edge extraction unit 611.

Figure 15:
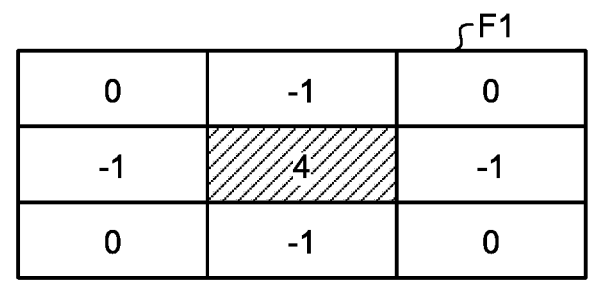

The edge extraction unit 611 uses a predetermined Laplacian filter to extract edge information from the ratio of pixel values input from the ratio calculation unit 610 and outputs this edge information to each of the binarization unit 613 and the threshold value calculation unit 612. Specifically, the edge extraction unit 611 uses the Laplacian filter F1 (3×3) illustrated in FIG. 15 to extract an edge with respect to the ratio of pixel values input from the ratio calculation unit 610. The Laplacian filter F1 illustrates edge extraction by four neighboring Laplacian filters. In edge extraction processing using the Laplacian filter F1, positive and negative values appear. Therefore, in the second embodiment, the edge intensity is represented by an absolute value.

The threshold value calculation unit 612 generates a histogram of the edge information input from the edge extraction unit 611, calculates a threshold value based on the histogram, and outputs the threshold value to the binarization unit 613.

The binarization unit 613 performs binarization processing that binarizes on the edge information input from the edge extraction unit 611 on the edge information input from the edge extraction unit 611 using the threshold value input from the threshold value calculation unit 612 and outputs the binarized information to the morphology processor 614.

The morphology processor 614 performs morphology processing on the binarized information input from the binarization unit 613 and outputs only a pixel (address of pixel) finally becoming 1 to the extraction unit 615. Note that the morphology processing executed by the morphology processor 614 will be described later.

The extraction unit 615 extracts a pixel having a feature included in the NB image based on the result input from the morphology processor 614 and the NB image input from the image generation unit 521. Specifically, the extraction unit 615 outputs the pixel having a feature included in the NB image to the first image composite unit 524 while maintaining a pixel value of a pixel of the NB image corresponding to a pixel position of the pixel finally becoming 1 by the morphology processing input from the morphology processor 614. Also, the extraction unit 615 outputs, as 0, a pixel value of a pixel of the NB image corresponding to a pixel position of a pixel finally becoming 0 by the morphology processing input from the morphology processor 614, to the first image composite unit 524.

Overview of Morphology Processing

Figure 16A:
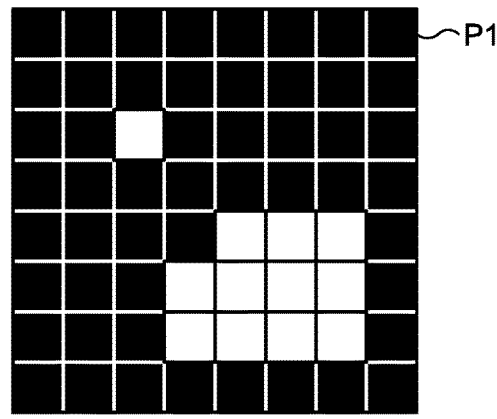
FIG. 16A is a diagram for schematically describing an overview of expansion processing of morphology processing according to the second embodiment.
Figure 16B:
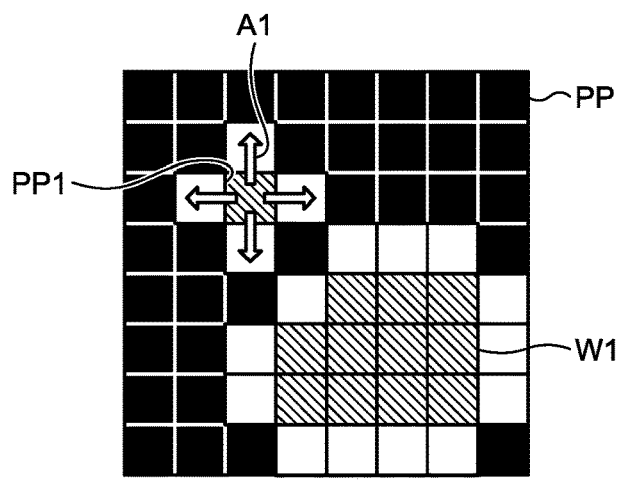
FIG. 16B is a diagram schematically illustrating an overview of the expansion processing by the morphology processing according to the second embodiment.
Figure 16C:
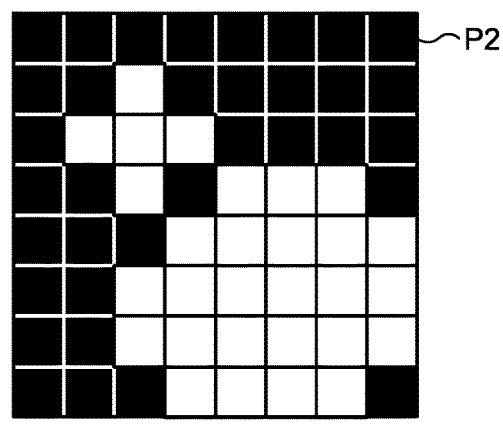
FIG. 16C is a diagram schematically illustrating an image after the expansion processing by the morphology processing according to the second embodiment.
Figure 17A:
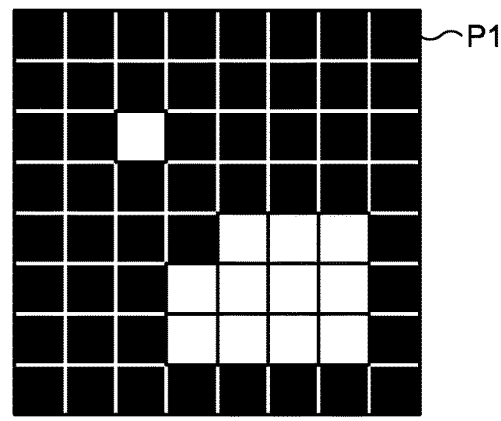
FIG. 17A is a diagram schematically illustrating an overview of contraction processing by the morphology processing according to the second embodiment.
Figure 17B:
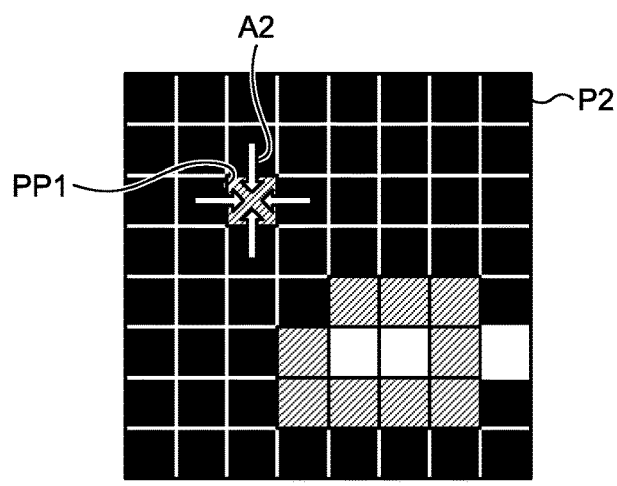
FIG. 17B is a diagram schematically illustrating an overview of the contraction processing by the morphology processing according to the second embodiment.
Figure 17C:
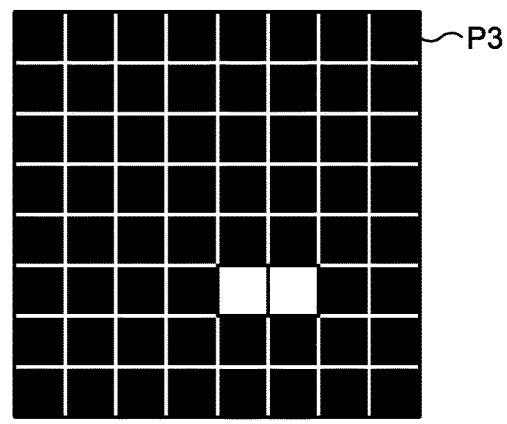
FIG. 17C is a diagram schematically illustrating an image after the contraction processing by the morphology processing according to the second embodiment.
Figure 18A:
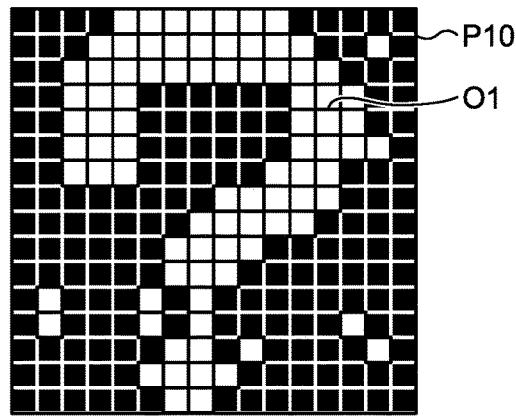
FIG. 18A is a diagram schematically illustrating a whole image of binarization before the morphology processing according to the second embodiment.
Figure 18B:
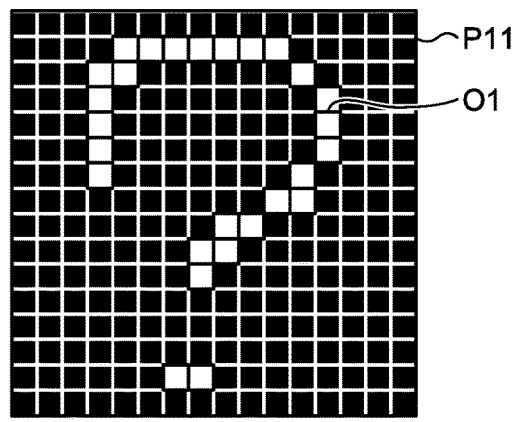
FIG. 18B is a diagram schematically illustrating a whole image after the contraction processing of the morphology processing according to the second embodiment.
Figure 18C:
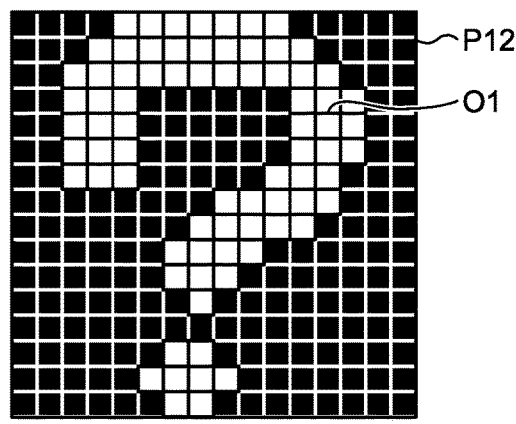
FIG. 18C is a diagram schematically illustrating a whole image after the expansion processing of the morphology processing according to the second embodiment.

Next, the morphology processing executed by the morphology processor 614 will be described in detail. FIGS. 16A to 16C are diagrams for schematically describing an overview of expansion processing of the morphology processing by the morphology processor 614. FIGS. 17A to 17C are diagrams for schematically describing an overview of contraction processing of the morphology processing by the morphology processor 614. FIGS. 18A to 18C are diagrams illustrating images of the morphology processing by the morphology processor 614.

As illustrated in FIGS. 16A to 16C, FIGS. 17A to 17C, and FIGS. 18A to 18C, the morphology processor 614 performs the morphology processing in which dilation processing that expands a figure in a binarized monochrome image by one pixel, or contraction processing that contracts the figure in the binarized monochrome image by one pixel is performed a plurality of times. In this way, the morphology processor 614 smooths a boundary between white and black of the binarized image expressed in black and white and removes (fills up) isolated points.

Specifically, in the case of performing the dilation processing, the morphology processor 614 dilates one pixel PP1 in a monochrome image P1 (original image) illustrated in FIG. 16A one pixel by one pixel in up and down (left and right) direction (see arrow A1), thereby generating an image P2 after the dilation processing (FIG. 16A→FIG. 16B→FIG. 16C).

Meanwhile, in the case of performing the contraction processing, the morphology processor 614 contracts one pixel PP1 in the monochrome image P1 (original image) illustrated in FIG. 17A one pixel by one pixel in the up and down (left and right) direction (see arrow A2), thereby generating an image P3 after the contraction processing (FIG. 17A→FIG. 17B→FIG. 17C).

Furthermore, the morphology processor 614 performs opening processing in which the above-described dilation processing is performed a predetermined number of times (for example, three times) after the above-described contraction processing is performed a predetermined number of times (for example, three times). Specifically, as illustrated in FIG. 18A, by performing the opening processing on a binarized monochrome image P10 to remove small pixels around a figure, only a figure to be extracted is left. In this way, it is possible to remove a protruding portion of the figure or separate a combining portion of the figure (FIG. 18A→FIG. 18B→FIG. 18C).

According to the second embodiment described above, as in the first embodiment, even in a case where a special light observation image is combined with a normal light observation image, a desired observation image can be obtained.

Third Embodiment

Next, a third embodiment will be described. The third embodiment is different from the configuration of the processor 5 according to the above-described first embodiment and different from the processing executed by the processor 5. Specifically, in the third embodiment, a coefficient when an NB image is combined with a B image is calculated, and a pixel of the NB image is multiplied by this coefficient, thereby being added to a B pixel. Hereinafter, a configuration of the endoscope system according to the third embodiment will be described and then the processing executed by the processor according to the third embodiment will be described. Note that the same components as those of the endoscope system 1 according to the above-described first embodiment are denoted by the same reference numerals, and the description thereof is omitted.

Configuration of Endoscope System

Figure 19:
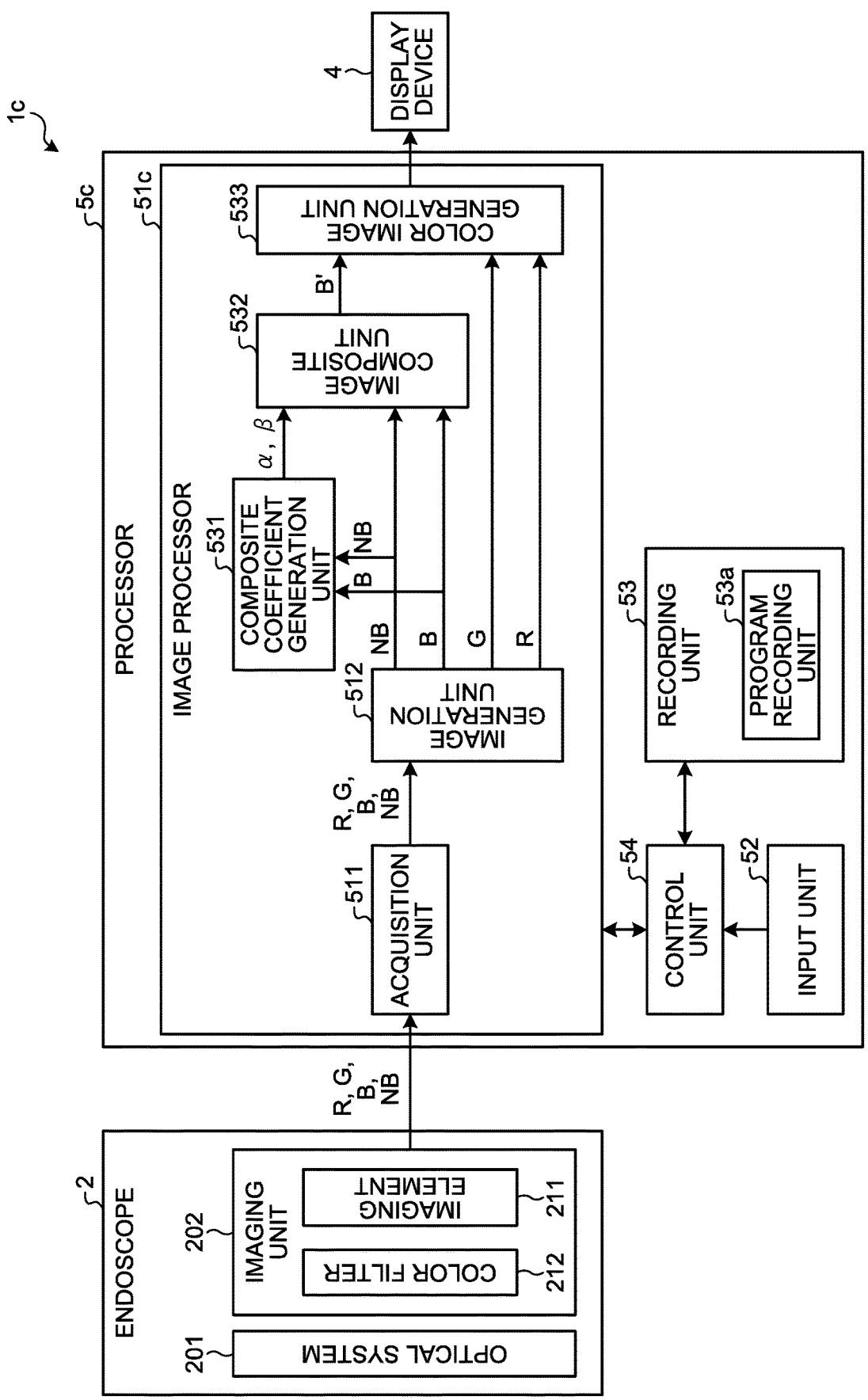
FIG. 19 is a block diagram illustrating functions of a main part of an endoscope system according to a third embodiment.

FIG. 19 is a block diagram illustrating functions of a main part of the endoscope system according to the third embodiment. An endoscope system 1c illustrated in FIG. 19 includes a processor 5c in place of the processor 5 according to the above-described first embodiment. Furthermore, the processor 5c includes an image processor 51c in place of the image processor 51 according to the above-described first embodiment.

The image processor 51c includes an acquisition unit 511, an image generation unit 512, a composite coefficient generation unit 531, an image composite unit 532, and a color image generation unit 533.

Based on the NB image and the B image input from the image generation unit 512, the composite coefficient generation unit 531 generates composite coefficients α and β for each of the NB image and the B image when the B image is combined with the NB image and outputs the composite coefficients α and β to the image composite unit 532.

Figure 20:
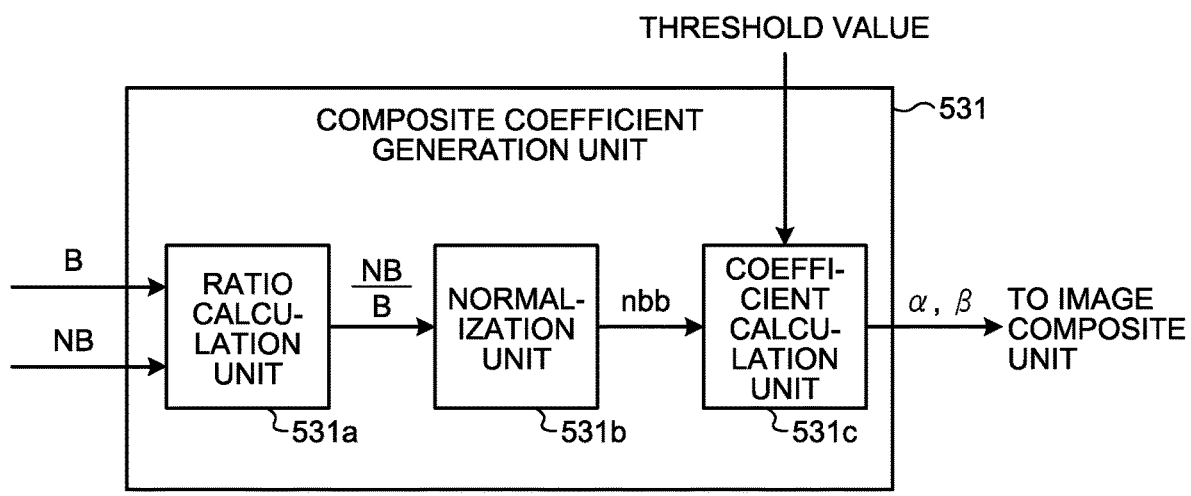
FIG. 20 is a block diagram illustrating a detailed configuration of a composite coefficient generation unit according to the third embodiment.

FIG. 20 is a block diagram illustrating a detailed configuration of the composite coefficient generation unit 531. As illustrated in FIG. 20, the composite coefficient generation unit 531 includes a ratio calculation unit 521a, a normalization unit 521b, and a coefficient calculation unit 521c.

The ratio calculation unit 521a calculates a ratio (NB/B) of a pixel value of the NB image to a pixel value of the B image for each pixel based on the NB image and the B image input from the image generation unit 512, and outputs this calculation result to the normalization unit 521b.

The normalization unit 521b normalizes the ratio for each pixel input from the ratio calculation unit 521a and outputs this normalization information nbb to the coefficient calculation unit 521c. In this case, the normalization unit 521b excludes an extreme numerical value, thereby normalizing the ratio for each pixel input from the ratio calculation unit 521a. At this time, the normalization unit 521b outputs, as 1.0, the normalization information nbb of the pixel, the extreme numerical value of which is excluded, to the coefficient calculation unit 521c.

Based on the normalization information nbb for each pixel input from the normalization unit 521b and a threshold value input from the outside, the coefficient calculation unit 521c calculates, for each pixel, a coefficient α for the NB image and a coefficient β for the B image when the B image is combined with the NB image. Specifically, in a case where the normalization information nbb for each pixel input from the normalization unit 521b is larger than the threshold value (the normalization information nbb>threshold value), the coefficient calculation unit 521c takes the value of the composite coefficient α to be multiplied by the pixel of the NB image as the ratio (NB/B) of the pixel value of the NB image to the pixel value of the B image and takes the value of the composite coefficient β to be multiplied by the pixel of the B image as 0. Meanwhile, in a case where the normalization information nbb for each pixel input from the normalization unit 521b is equal to or less than the threshold value (the normalization information nbb threshold value), the coefficient calculation unit 521c takes the value of the composite coefficient α to be multiplied by the pixel of the NB image as 0 and takes the value of the composite coefficient β to be multiplied by the pixel of the B image as 1.

Referring back to FIG. 19, the description of the configuration of the image processor 51c will be continued.

Based on the composite coefficients α and β generated by the composite coefficient generation unit 531, the image composite unit 532 combines the NB image and the B image input from the image generation unit 512 to generate a composite image B' and outputs the composite image B' to the color image generation unit 533. Specifically, the image composite unit 532 calculates a pixel value of the composite image B' for each pixel by the following equation (1).

$$B'=\alpha \times NB + \beta \times B \qquad (1)$$

The color image generation unit 533 generates a color image based on the composite image B' input from the image composite unit 532 and the G image and the R image that are input from the image generation unit 512 and outputs the color image to a display device 4.

Processing by Processor

Figure 21:
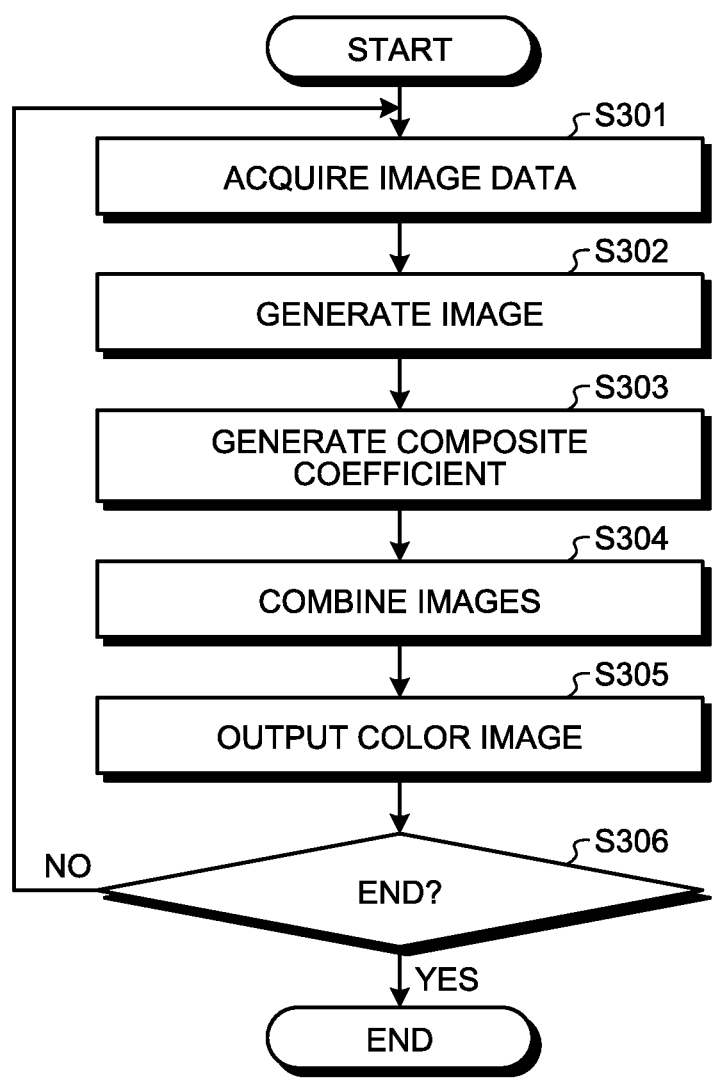
FIG. 21 is a flowchart illustrating an overview of processing executed by a processor according to the third embodiment.

Next, processing executed by the processor 5c will be described. FIG. 21 is a flowchart illustrating an overview of the processing executed by the processor 5c. In FIG. 21, steps S301 and S302 correspond to steps S101 and S102 of above-described FIG. 8, respectively.

In step S303, based on the NB image and the B image that are input from the image generation unit 512, the composite coefficient generation unit 531 generates, a composite coefficient of each of the NB image and the B image when the B image is combined with the NB image for each pixel and outputs the composite coefficients α and β to the image composite unit 532.

Subsequently, based on the composite coefficients α and β generated by the composite coefficient generation unit 531, the image composite unit 532 combines the NB image and the B image that are input from the image generation unit 512 for each pixel to generate a composite image B' and outputs the composite image B' to the color image generation unit 533 (step S304).

Thereafter, the color image generation unit 533 generates a color image based on the image B' input from the image composite unit 532 and the G image and the R image that are input from the image generation unit 512 and outputs the color image to the display device 4 (step S305).

According to the third embodiment described above, as in the first embodiment, even in a case where a special light observation image is combined with a normal light observation image, a desired observation image can be obtained.

Note that in the third embodiment, after the above-described morphology processing according to the second embodiment is performed on the NB image, the normalization unit 521b generates the normalization information nbb, and as a result of the morphology processing, the value of the composite coefficient α to be multiplied by the remaining pixel is taken as the ratio (NB/B) of the pixel value of the NB image to the pixel value of the B image, and the value of the composite coefficient β to be multiplied by the pixel of the B image is taken as 0. Meanwhile, in the case of other pixels as a result of the morphology processing, the value of the composite coefficient α to be multiplied by the pixel of the NB image may be taken as 0 and the value of the composite coefficient β multiplied by the pixel of the B image may be taken as 1.

Other Embodiments

In the first to third embodiments, the endoscopes 2 and 2a, the display device 4, the input unit 52, the recording unit 53, and the control unit 54 are provided in the endoscope systems 1, 1a, and 1c. However, these constituent elements may be removed without departing from the gist of the disclosure. Furthermore, variations can be formed by appropriately combining a plurality of constituent elements disclosed in the above-described first to third embodiments. For example, some constituent elements may be removed from all the constituent elements in the above-described first to third embodiments. Furthermore, the constituent elements described in the above-described first to third embodiments may be appropriately combined.

In the embodiments, the above-described "unit" can be replaced with "means", "circuit", or the like. For example, the control unit can be replaced with a control means or a control circuit.

Furthermore, in the embodiments, the image data is transmitted to the image processing apparatus via a transmission cable. However, for example, the image data does not need to be transmitted in a wired manner, but the image data may be transmitted in a wireless manner. In this case, image data or the like may be transmitted to the image processing apparatus according to a predetermined wireless communication standard (for example, Wireless Fidelity (Wi-Fi) (registered trademark) or Bluetooth (registered trademark)). Of course, wireless communication may be performed according to other wireless communication standards.

In the embodiments, the light source device and the image processing apparatus (processor) are formed separately, but the present disclosure is not limited to this configuration. For example, a configuration in which an image processing apparatus and a light source are integrally formed may be adopted.

Furthermore, in the embodiments, the simultaneous lighting endoscopes have been described as examples, but even if the endoscope is a sequential lighting endoscope, the sequential lighting endoscope can be applied. Furthermore, in the embodiments, even if the endoscope is an endoscope capable of emitting predetermined narrow band light other than the narrow band light, the endoscope emitting predetermined narrow band light other than the narrow band light can be applied. Moreover, in the embodiments, even if the endoscope is a flexible endoscope (upper and lower endoscope), a sinus endoscope and a capsule endoscope in addition to a rigid endoscope, the flexible endoscope, the sinus endoscope and the capsule endoscope can be applied.

Furthermore, in the embodiments, the endoscope is inserted into the subject. However, even if the endoscope is, for example, a capsule endoscope or an imaging apparatus that captures an image of a subject, the capsule endoscope or imaging apparatus can be applied.

Note that in the description of the flowcharts in the present specification, a relationship between before and after each processing is clearly indicated using expressions such as "first", "thereafter", and "subsequently". However, the order of the processing necessary for carrying out the present disclosure is not uniquely determined by these expressions. That is, the order of the processing in the flowcharts described in the present specification can be changed within a range without inconsistency.

According to the present disclosure, it is possible to achieve an effect that a normal light observation image and a special light observation image that are synchronized temporally and spatially are generated and are combined with each other, whereby a desired observation image can be obtained.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An image processing apparatus comprising:
    a processor comprising hardware, the processor being configured to execute:
        acquiring image data generated by an imaging device having a predetermined array pattern including a first pixel configured to receive light in a red wavelength band, a second pixel configured to receive light in a green wavelength band, a third pixel configured to receive light in a blue wavelength band, and a fourth pixel configured to receive at least one of: narrow band light in a wavelength band that is the green wavelength band and narrower than the green wavelength band; and narrow band light in a wavelength band that is the blue wavelength band and narrower than the blue wavelength band;
        generating, by performing demosaicing processing of interpolating a pixel value to the acquired image data, a first interpolation image data corresponding to the light in the red wavelength band, a second interpolation image data corresponding to the light in the green wavelength band, a third interpolation image data corresponding to the light in the blue wavelength band, and fourth interpolation image data corresponding to the narrow band light;
        calculating: a ratio of a pixel value of the fourth interpolation image data to a pixel value of the second interpolation image data for each region including one or a plurality of pixels based on the second interpolation image data and the fourth interpolation image data corresponding to the narrow band light in the wavelength band that is the green wavelength band and narrower than the green wavelength band; or a ratio of a pixel value of the fourth interpolation image data to a pixel value of the third interpolation image data for each region including one or a plurality of pixels based on the third interpolation image data and the fourth interpolation image data corresponding to the narrow band light in the wavelength band that is the blue wavelength band and narrower than the blue wavelength band;

extracting a pixel of the fourth interpolation image data in the region where the calculated ratio exceeds a predetermined threshold value;

generating a composite image data based on at least one of: the pixel value of the extracted pixel of the fourth interpolation image data corresponding to the narrowband light in the wavelength band that is the green wavelength band and narrower than the green wavelength band and the second interpolation image data; and the extracted pixel value of the pixel of the fourth interpolation image data corresponding to the narrow band light in the wavelength band that is the blue wavelength band and narrower than the blue wavelength band and the third interpolation image data; and generating color image data based on the generated composite image data, the first interpolation image data, and at least one of the second interpolation image data and the third interpolation image data.

2. The image processing apparatus according to claim 1, wherein the processor weights and adds the pixel value of the extracted pixel to at least one of the second interpolation image data and the third interpolation image data to generate the composite image data.

3. The image processing apparatus according to claim 1, wherein the processor is configured to further execute:

generating luminance image data and chromaticity image data by converting the first interpolation image data, the second interpolation image data, and the third interpolation image data into coordinates in a color space, weighting and adding the pixel value of the extracted pixel to the luminance image data to generate the composite image data, and generating the color image data based on the composite image data and the chromaticity image data.

4. The image processing apparatus according to claim 1, wherein the processor is configured to further execute:

calculating a ratio of the pixel value of the fourth interpolation image data to the pixel value of the second interpolation image data and a pixel value of the third interpolation image data for each region, based on the fourth interpolation image data and at least one of the generated second interpolation image data and the generated third interpolation image data;

determining whether the calculated ratio exceeds the predetermined threshold value; and extracting the pixel of the fourth interpolation image data, the ratio of which is determined as a ratio exceeding the predetermined threshold value.

5. The image processing apparatus according to claim 4, wherein the processor calculates the ratio of the pixel value of the fourth interpolation image data to the pixel value of the second interpolation image data and the pixel value of the third interpolation image data for each pixel, based on the fourth interpolation image data and at least one of the generated second interpolation image data and the generated third interpolation image data.

6. The image processing apparatus according to claim 4, wherein the processor divides each of the fourth interpolation image data and at least one of the second interpolation image data and the third interpolation image data into a plurality of blocks every predetermined number of pixels and calculates a ratio of an average value of pixel values of respective pixels included in the plurality of blocks of the fourth interpolation image data to an average value of pixel values of respective pixels included in the plurality of blocks of at least one of the second interpolation image data and the third interpolation image data for each block, and the processor extracts the pixel included in the block of the fourth interpolation image data, the ratio of which is determined as a ratio exceeding the predetermined threshold value.

7. The image processing apparatus according to claim 4, wherein the processor is configured to further execute calculating the predetermined threshold value based on a histogram of the calculated ratio.

8. An image processing method executed by an image processing apparatus, the method comprising:

acquiring image data generated by an imaging device having a predetermined array pattern including a first pixel configured to receive light in a red wavelength band, a second pixel configured to receive light in a green wavelength band, a third pixel configured to receive light in a blue wavelength band, and a fourth pixel configured to receive at least one of: narrow band light in a wavelength band that is the green wavelength band and narrower than the green wavelength band; and narrow band light in a wavelength band that is the blue wavelength band and narrower than the blue wavelength band;

generating, by performing demosaicing processing of interpolating a pixel value to the acquired image data, a first interpolation image data corresponding to the light in the red wavelength band, a second interpolation image data corresponding to the light in the green wavelength band, a third interpolation image data corresponding to the light in the blue wavelength band, and fourth interpolation image data corresponding to the narrow band light;

calculating: a ratio of a pixel value of the fourth interpolation image data to a pixel value of the second interpolation image data for each region including one or a plurality of pixels based on the second interpolation image data and the fourth interpolation image data corresponding to the narrow band light in the wavelength band that is the green wavelength band and narrower than the green wavelength band; or a ratio of a pixel value of the fourth interpolation image data to a pixel value of the third interpolation image data for each region including one or a plurality of pixels based on the third interpolation image data and the fourth interpolation image data corresponding to the narrow band light in the wavelength band that is the blue wavelength band and narrower than the blue wavelength band;

extracting a pixel of the fourth interpolation image data in the region where the calculated ratio exceeds a predetermined threshold value;

generating a composite image data based on at least one of: the pixel value of the extracted pixel of the fourth interpolation image data corresponding to the narrowband light in the wavelength band that is the green wavelength band and narrower than the green wavelength band and the second interpolation image data; and the extracted pixel value of the pixel of the fourth interpolation image data corresponding to the narrow band light in the wavelength band that is the blue wavelength band and narrower than the blue wavelength band and the third interpolation image data; and generating color image data based on the generated composite image data, the first interpolation image data, and at least one of the second interpolation image data and the third interpolation image data.

9. A non-transitory computer readable recording medium on which an executable program is recorded, the program instructing a processor of an image processing apparatus to execute:

acquiring image data generated by an imaging device having a predetermined array pattern including a first pixel configured to receive light in a red wavelength band, a second pixel configured to receive light in a green wavelength band, a third pixel configured to receive light in a blue wavelength band, and a fourth pixel configured to receive at least one of: narrow band light in a wavelength band that is the green wavelength band and narrower than the green wavelength band; and narrow band light in a wavelength band that is the blue wavelength band and narrower than the blue wavelength band;

generating, by performing demosaicing processing of interpolating a pixel value to the acquired image data, a first interpolation image data corresponding to the light in the red wavelength band, a second interpolation image data corresponding to the light in the green wavelength band, a third interpolation image data corresponding to the light in the blue wavelength band, and fourth interpolation image data corresponding to the narrow band light;

calculating: a ratio of a pixel value of the fourth interpolation image data to a pixel value of the second interpolation image data for each region including one or a plurality of pixels based on the second interpolation image data and the fourth interpolation image data corresponding to the narrow band light in the wavelength band that is the green wavelength band and narrower than the green wavelength band; or a ratio of a pixel value of the fourth interpolation image data to a pixel value of the third interpolation image data for each region including one or a plurality of pixels based on the third interpolation image data and the fourth interpolation image data corresponding to the narrow band light in the wavelength band that is the blue wavelength band and narrower than the blue wavelength band;

extracting a pixel of the fourth interpolation image data in the region where the calculated ratio exceeds a predetermined threshold value;

generating a composite image data based on at least one of: the pixel value of the extracted pixel of the fourth interpolation image data corresponding to the narrow-band light in the wavelength band that is the green wavelength band and narrower than the green wavelength band and the second interpolation image data; and the extracted pixel value of the pixel of the fourth interpolation image data corresponding to the narrow band light in the wavelength band that is the blue wavelength band and narrower than the blue wavelength band and the third interpolation image data; and generating color image data based on the generated composite image data, the first interpolation image data, and at least one of the second interpolation image data and the third interpolation image data.

* * * * *